(12) United States Patent
Yamamoto

(10) Patent No.: US 9,789,244 B2
(45) Date of Patent: Oct. 17, 2017

(54) INJECTOR HEAD WITH ROTATION MECHANISM

(75) Inventor: Tetsuya Yamamoto, Osaka (JP)

(73) Assignee: SUGAN CO., LTD., Osaka (JP)

( * ) Notice: Subject to any disclaimer, the term of this patent is extended or adjusted under 35 U.S.C. 154(b) by 762 days.

(21) Appl. No.: 14/350,014

(22) PCT Filed: Oct. 5, 2011

(86) PCT No.: PCT/JP2011/072977
§ 371 (c)(1),
(2), (4) Date: Apr. 4, 2014

(87) PCT Pub. No.: WO2013/051115
PCT Pub. Date: Apr. 11, 2013

(65) Prior Publication Data
US 2014/0249412 A1    Sep. 4, 2014

(51) Int. Cl.
*A61M 5/00* (2006.01)
*A61M 5/145* (2006.01)
*A61M 39/28* (2006.01)
*A61M 39/22* (2006.01)
(Continued)

(52) U.S. Cl.
CPC ............ *A61M 5/007* (2013.01); *A61M 5/145* (2013.01); *A61M 5/14546* (2013.01); *A61M 39/285* (2013.01); *A61M 39/223* (2013.01); *A61M 39/225* (2013.01); *A61M 2005/1402* (2013.01); *A61M 2005/1403* (2013.01); *A61M 2039/0018* (2013.01)

(58) Field of Classification Search
CPC .............. A61M 5/007; A61M 5/14546; A61M 39/285; A61M 2005/1402; A61M 2005/1403; A61M 1005/14573
See application file for complete search history.

(56) References Cited

U.S. PATENT DOCUMENTS

| 4,695,271 A * | 9/1987 | Goethel ................ A61M 5/007 |
| | | 128/DIG. 1 |
| 5,830,194 A | 11/1998 | Anwar et al. |
| 5,968,015 A | 10/1999 | Yamamoto |
| 6,004,285 A | 12/1999 | Sugahara |
| 2003/0117888 A1 | 6/2003 | Reilly et al. |

(Continued)

FOREIGN PATENT DOCUMENTS

| EP | 1829576 A1 | 9/2007 |
| JP | 10165396 A | 6/1998 |

(Continued)

OTHER PUBLICATIONS

Chinese Notification on the First Office Action dated May 21, 2015 in corresponding Chinese Patent Application No. 2011800740141 (English translation).

(Continued)

*Primary Examiner* — Nathan R Price
*Assistant Examiner* — Melissa A Snyder
(74) *Attorney, Agent, or Firm* — McDermott Will & Emery LLP

(57) ABSTRACT

An injector head with rotation mechanism allows selection between a state in which a syringe assumes a priming orientation with a through hole of the syringe positioned upper than the injector head body, and a state in which the syringe assumes a contrast agent injectable orientation with the through hole of the syringe positioned lower than the injector head body.

4 Claims, 25 Drawing Sheets

(51) Int. Cl.
 *A61M 5/14* (2006.01)
 *A61M 39/00* (2006.01)

(56) References Cited

U.S. PATENT DOCUMENTS

| | | | | |
|---|---|---|---|---|
| 2005/0004447 | A1* | 1/2005 | Yamamoto | A61M 5/16827 600/420 |
| 2005/0049556 | A1* | 3/2005 | Tanaka | A61M 5/14546 604/152 |
| 2005/0123895 | A1* | 6/2005 | Freund | A61B 17/32002 435/2 |
| 2006/0184124 | A1 | 8/2006 | Cowan et al. | |

FOREIGN PATENT DOCUMENTS

| | | |
|---|---|---|
| JP | 10-244002 A | 9/1998 |
| WO | 2011/011346 A1 | 1/2011 |

OTHER PUBLICATIONS

Microfilm of the specification and drawings annexed to the request of Japanese Utility Model Application No. 71326/1971 (Laid-open No. 31890/1973) (Tokyo Shibaura Electric Co., Ltd.), Apr. 18, 1973 (Apr. 18, 1973).
International Search Report issued in Application No. PCT/JP2011/072977 dated Dec. 20, 2011.
Japanese Notice of Allowance issued in Application No. 2013-537318 dated Jun. 2, 2015, with English Translation.
Extended European Search Report issued in Application No. 11873723.8 dated Jun. 8, 2015.

\* cited by examiner

INJECTOR HEAD WITH ROTATION MECHANISM

CROSS-REFERENCE TO RELATED APPLICATIONS

The present application is the U.S. National Phase of PCT/JP2011/072977 dated Oct. 5, 2011; the subject matter of each is incorporated herein by reference in entirety.

TECHNICAL FIELD

The present invention relates to an injector head for introducing contrast agent or other chemical to a patient and, more specifically, to an injector head with rotation mechanism, having a mechanism allowing rotation of the injector head in a prescribed direction.

BACKGROUND ART

In a cardiac catheter test, a contrast agent is introduced to a patient using an injector head, and the test is done while imaging the affected part. Utilizing a coronary angiography of providing images of cardiac blood vessels, an operation of blood vessel is performed for widening a narrowed lesion by catheter method. Utilizing left ventricular angiogram imaging the left ventricle of the heart, behavior of cardiac muscle around the left ventricle is tested, by monitoring systole and diastole states of the heart.

Examples of such an injector head are disclosed, for example, in Japanese Patent Laying-Open Nos. 10-165396 (Patent Document 1) and 10-244002 (Patent Document 2).

When a test is to be conducted using an injector head, an operation referred to as "priming" is required, for expelling air from a syringe attached to the injector head in advance.

At the time of priming, in order to efficiently expel air from the syringe, it is necessary to have the injector head assume an upward facing orientation (priming orientation), so that a through hole provided at the front end of the syringe faces upward.

On the other hand, when introducing a contrast agent to the patient, the injector head must be rotated broadly to have the injector head in a downward facing orientation (contrast agent injectable orientation), so that the through hole provided at the front end of the syringe faces downward.

To the through hole provided at the front end of the syringe, a tube leading to the patient is coupled. When an operator selects the priming orientation or the contrast agent injectable orientation of the injector head, the injector head is rotated broadly with the tube kept coupled to the through hole of the injector head.

If the injector head is rotated broadly, the tube coupled to the through hole of the syringe also swings significantly. Therefore, the tube must have a margin in its length. If the tube is adapted to have an enough margin in length, the engineer or operator must be very careful to avoid any contact between the tube and other devices. In order to avoid contact between the tube and other devices, arrangement of devices must also be taken care of.

CITATION LIST

Patent Document

PTD 1: Japanese Patent Laying-Open No. 10-165396
PTD 2: Japanese Patent Laying-Open No. 10-244002

SUMMARY OF INVENTION

Technical Problem

The problem to be solved by the present invention is that when the injector head is moved between the "priming orientation" and the "contrast agent injectable orientation," care must be taken to prevent interference between the tube coupled to the injector head and other devices.

The present invention was made to solve the above-described problem, and its object is to provide an injector head with rotation mechanism having a structure reducing possibility of interference between the tube coupled to the injector head and other devices even when the injector head is moved between the "priming orientation" and the "contrast agent injectable orientation."

Solution to Problem

The present invention provides an injector head with rotation mechanism, including: a supporting part; a rotating part fixed on the supporting part with its rotation axis extending substantially horizontally; an injector head body fixed on the rotating part to be rotatable about the rotation axis; and a syringe detachably attached to the injector head body.

The syringe includes a through hole at a front end side; in a state where the syringe is attached to the injector head body, when viewed from the direction perpendicular to and parallel to the rotation axis, central axis line of the syringe is inclined with respect to the rotation axis; and by rotating the injector head body about the rotation axis as the center of rotation, selection is possible between a state in which the syringe assumes the priming orientation with the through hole side of the syringe positioned upper than the injector head body and a state in which the syringe assumes the contrast agent injectable orientation with the through hole side of the syringe positioned lower than the injector head body.

According to another aspect, the through hole is provided at a position eccentric to the central axis line of the syringe; and the syringe is mounted on the injector head body such that when the syringe is in the priming orientation, the through hole is positioned at the uppermost position, and when the syringe is in the contrast agent injectable orientation, the through hole is positioned at the lowermost position.

According to a further aspect, the injector head body has a substantially rectangular parallelepiped shape; the syringe is mounted on a first surface of the injector head body; the rotating part is fixed on an upper corner area of a second surface opposite to the first surface; in the priming orientation, a third surface positioned on the upper side between the first and the second surfaces is inclined upward from the side of the second surface to the side of the first surface; and in the contrast agent injectable orientation with the injector head body rotated about the rotation axis as the center of rotation, a fourth surface positioned on the lower side between the first surface and the second surface is inclined downward from the side of the second surface to the side of the first surface.

According to a further aspect, the syringe has first and second syringes; the first syringe is mounted on the injector head body such that in the priming orientation, when viewed from the direction perpendicular to and parallel to the rotation axis, the axis of the first syringe intersects the rotation axis on the side of the through hole of the first syringe, and in the contrast agent injectable orientation, when viewed from the direction perpendicular to and parallel to the rotation axis, the axis of the first syringe intersects the rotation axis on the side of the injector head body of the first syringe.

The second syringe described above is mounted on the injector head body such that in the priming orientation, when viewed from the direction perpendicular to and parallel to the rotation axis, the axis of the second syringe intersects the rotation axis on the side of the injector head body of the second syringe, and in the contrast agent injectable orientation, when viewed from the direction perpendicular to and parallel to the rotation axis, the axis of the second syringe intersects the rotation axis on the side of the through hole of the second syringe.

According to another aspect, the injector head with rotation mechanism further includes: a tube assembly coupled to the side of a patient; and a flow path switching device having one end detachably connected to the tube assembly and the other end connected to the first and second syringes, for switching the tube assembly to be communicated with the first syringe or with the second syringe.

The tube assembly described above is used one time for one patient; and the injector head body, the first and second syringes, and the flow path switching device are used for a plurality of patients.

Advantageous Effects of Invention

By the injector head with rotation mechanism, the injector head with rotation mechanism having a structure reducing possibility of interference between the tube coupled to the injector head and other devices even when the injector head is moved between the "priming orientation" and the "contrast agent injectable orientation" can be provided.

DESCRIPTION OF EMBODIMENTS

Figure 1:
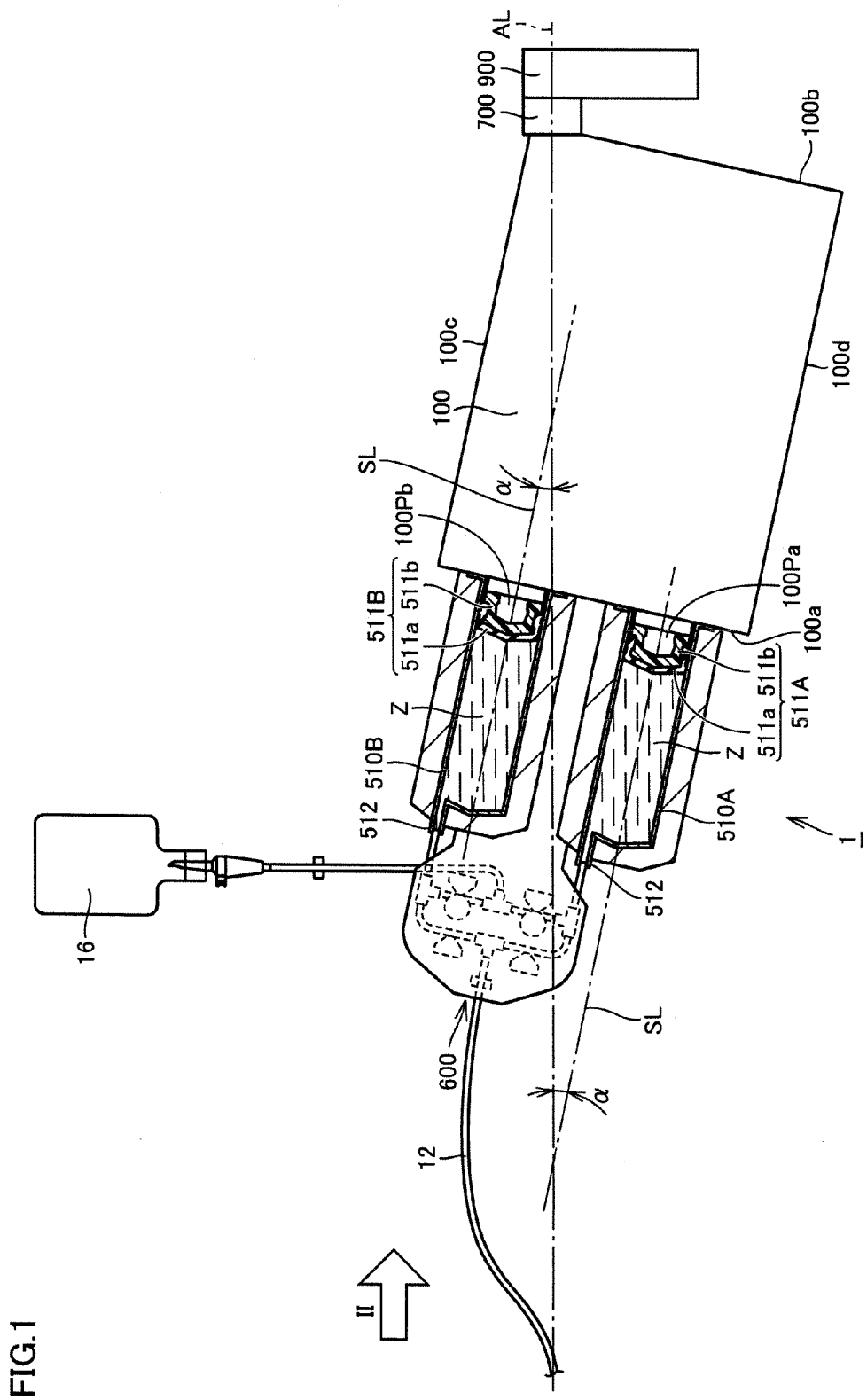
FIG. 1 is a side view showing the injector head with rotation mechanism (in priming orientation) in accordance with an embodiment.

In the following, the injector head with rotation mechanism based on the present invention will be described. In the embodiments described below, the same or corresponding components will be denoted by the same reference characters, and description thereof may not be repeated. Any numbers and amounts mentioned are not limiting the scope of the invention, unless specifically described to the contrary.

In the figures, for easier understanding of the contrast agent in the syringe, piston position and plunger position, the syringe is shown in cross-sections. The priming orientation refers to a state for performing a preliminary work (such as filling the syringe with the contrast agent) before injecting the contrast agent, and the contrast agent injectable orientation refers to the orientation ready to start injection of the contrast agent and the orientation during injection of the contrast agent.

(Injector Head 1 with Rotation Mechanism)

Figure 2:
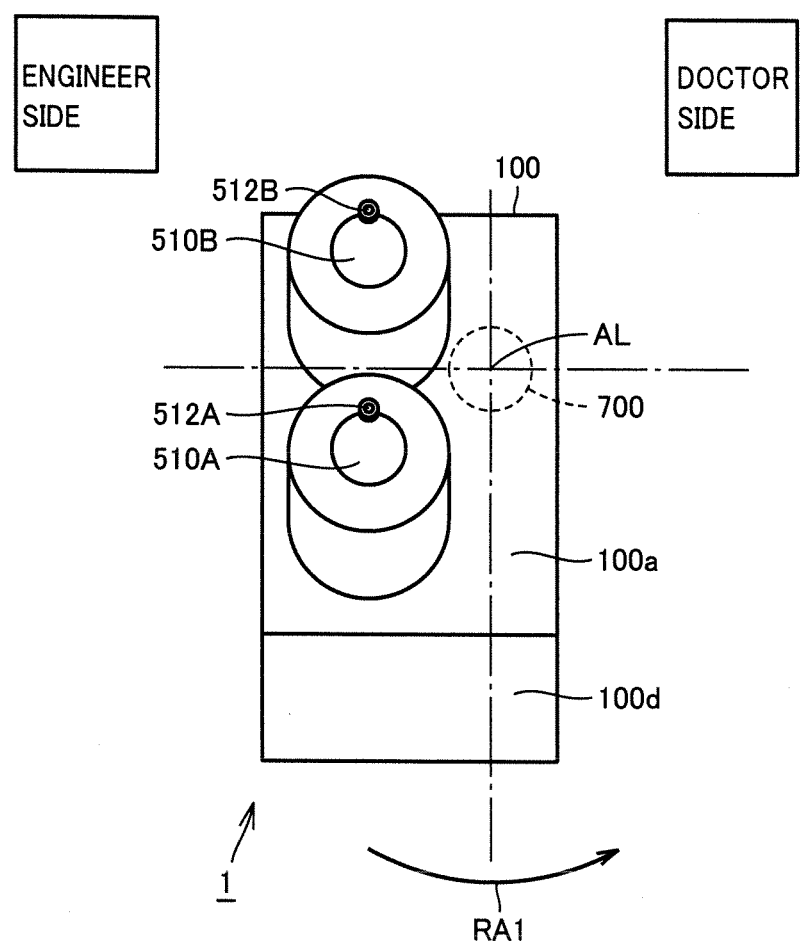
FIG. 2 is a view from a direction of an arrow II of FIG. 1.
Figure 3:
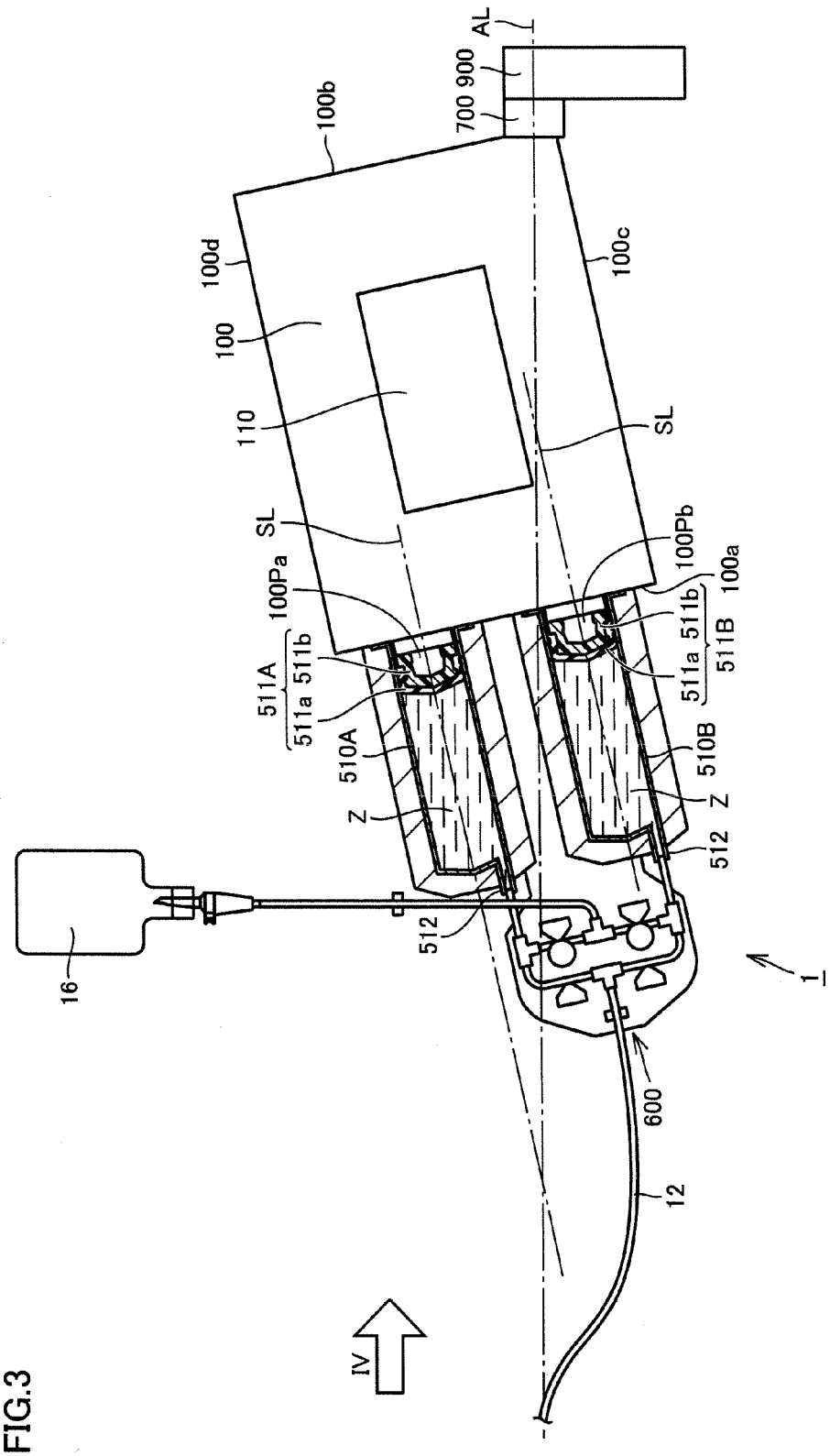
FIG. 3 is a side view showing the injector head with rotation mechanism (in contrast agent injectable orientation) in accordance with an embodiment.
Figure 4:
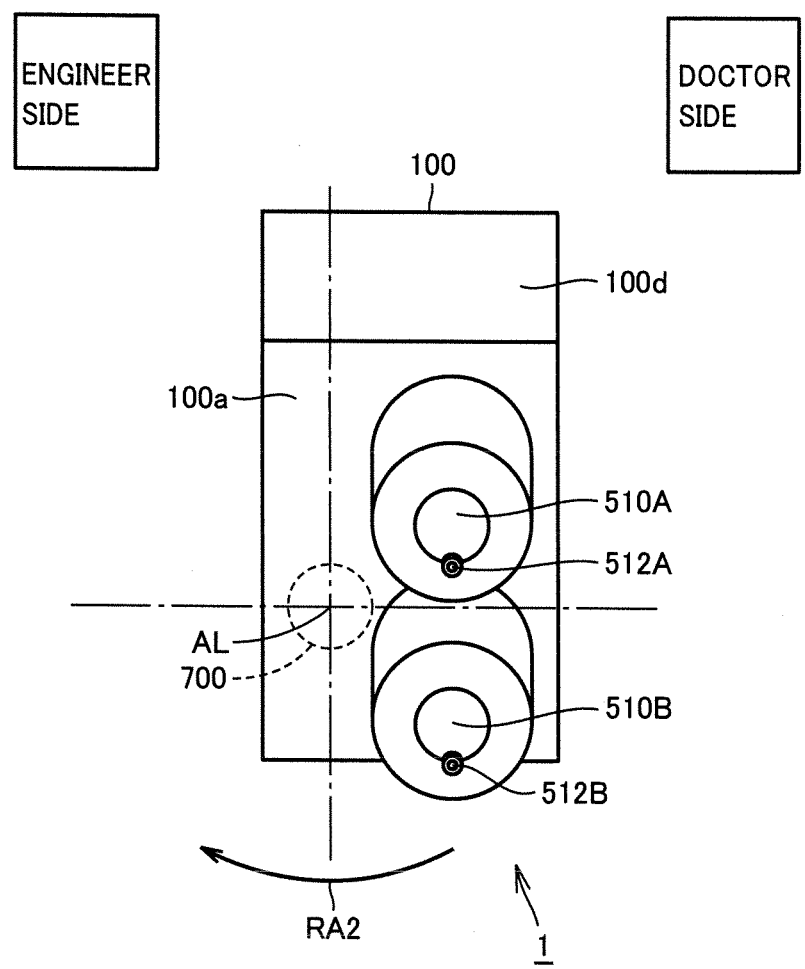
FIG. 4 is a view from a direction of an arrow IV of FIG. 3.
Figure 5:
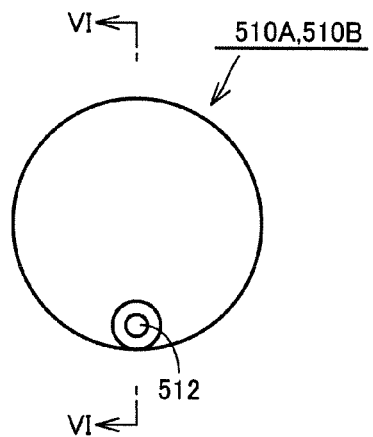
FIG. 5 is a side view from a direction of an arrow V of FIG. 6, of the syringe attached to the injector head with rotation mechanism in accordance with an embodiment.
Figure 6:
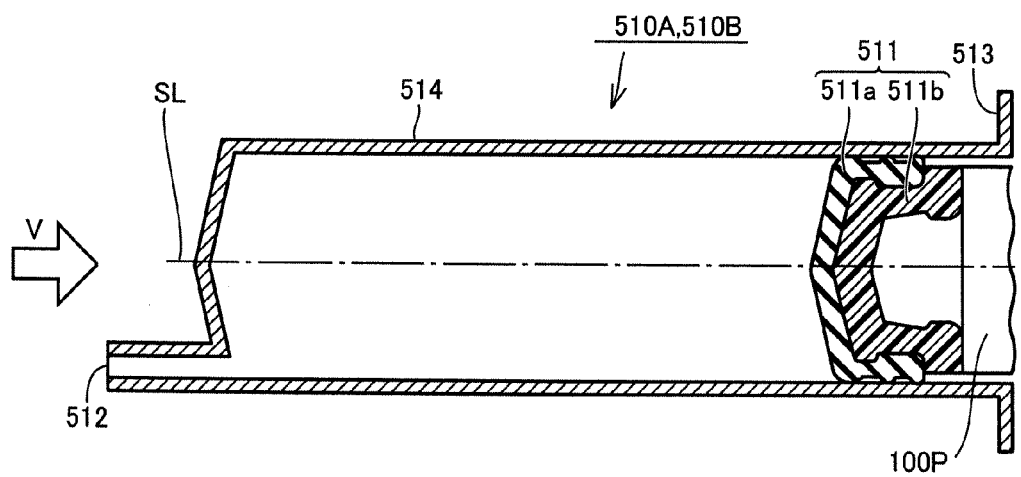
FIG. 6 is a cross-sectional view taken along the line VI-VI of FIG. 5, of the syringe attached to the injector head with rotation mechanism in accordance with an embodiment.

Referring to FIGS. 1 to 6, injector head 1 with rotation mechanism in accordance with an embodiment of the present invention will be described. FIG. 1 is a side view showing injector head 1 with rotation mechanism (in priming orientation), FIG. 2 is a view from a direction of an arrow II of FIG. 1, FIG. 3 is a side view showing injector head 1 with rotation mechanism (in contrast agent injectable orientation), and FIG. 4 is a view from a direction of an arrow IV of FIG. 3. FIG. 5 is a side view of a syringe 510 from a direction of an arrow V of FIG. 6, and FIG. 6 is a cross-sectional view taken along the line VI-VI of FIG. 5.

Injector head 1 with rotation mechanism includes: a support post 900 as a supporting part; a rotating part 700 fixed on support post 900 to have its rotation axis AL extending substantially horizontally; an injector head body 100 fixed to rotating part 700 to be rotatable about the rotation axis AL; and first and second syringes 510A and 510B detachably attached to injector head body 100. A roller bearing or the like is used for rotating part 700.

To a through hole 512 formed at the front end portion of each of the first and second syringes 510A and 510B, a first flow path switching device 600 is coupled. Details of the first flow path switching device 600 will be described later. On a side surface of injector head body 100, an operation monitor 110 implemented by a touch-panel is provided (see FIG. 3).

As the first and second syringes 510A and 510B, a syringe having such a shape as shown in FIGS. 5 and 6 is used. The syringe has a cylindrical part 514 having front end side closed and back end opened to receive a piston 511 to be fit in liquid-tight manner, a through hole 512 provided on the front end side, and a flange provided at the back end side.

Piston 511 includes a piston rubber 511a and a piston core 511b covered by piston rubber 511a. To piston core 511b, a plunger 100P provided inside injector head 100 is coupled. Cylindrical part 514 is fixed on injector head body 100.

As plunger 100P moves forward and backward, piston 511 also moves forward/backward in cylindrical part 514. Piston rubber 511a moves while maintaining liquid-tightness with respect to the inner circumferential surface of cylindrical part 514.

Syringe 510 in accordance with the present embodiment has a through hole 512 at a position eccentric from the central axis line SL of syringe 510. The central axis line of syringe 510 means a phantom line extending from the front side to the back side passing through the central axis of syringe 510.

Again referring to FIGS. 1 to 4, in the present embodiment, in a state where the first and second syringes 510A and 510B are attached to injector head body 100, when viewed from a direction perpendicular to and parallel to the rotation axis AL (in a direction perpendicular to the drawing sheet), the central axis lines SL of the first and second syringes 510A and 510B are inclined from rotation axis AL.

When viewed from the direction perpendicular to and parallel to the rotation axis AL (in a direction perpendicular to the drawing sheet), the angle ($\alpha$) at which the central axis line SL and the rotation axis AL intersect is about 5 to about 30 degrees, preferably about 7 to about 25 degrees, and more preferably, about 10 to about 15 degrees.

Specifically, referring to FIG. 1, injector head body 100 has a substantially rectangular parallelepiped shape, the first and second syringes 510A and 510B are attached to a first surface 100a of injector head body 100, and rotating part 700 is fixed to an area at an upper corner (near the third surface 100c) of a second surface 100b opposite to the first surface 100a. In the shown example, the first and second syringes 510A and 510B are filled with contrast agent Z.

In the priming orientation shown in FIGS. 1 and 2, a third surface 100c positioned on the upper side between the first and second surfaces 100a and 100b is inclined upward from the side of the second surface 100b to the side of the first surface 100a, and a fourth surface 100d positioned on the lower side between the first and second surfaces 100a and 100b is also inclined upward from the side of the second surface 100b to the side of the first surface 100a.

Further, in the priming orientation, the first and second syringes 510A and 510B are attached to injector head body 100 such that through hole 512 of each of the first and second syringes 510A and 510B is positioned at the uppermost side.

Referring to FIGS. 3 and 4, in the contrast agent injectable orientation with injection head body 100 rotated (in the direction of an arrow RA1 of FIG. 2) about the rotation axis AL as the center of rotation, the fourth surface 100d positioned on the upper side between the first and second surfaces 100a and 100b is inclined downward from the side of the second surface 100b to the side of the first surface 100a, and the fourth surface 100d positioned on the lower side between the first and second surfaces 100a and 100b is also inclined downward from the side of the second surface 100b to the side of the first surface 100a.

By rotating injector head body 100 about the rotation axis AL as the center of rotation, injector head 1 with rotation mechanism in accordance with the present embodiment can selectively be set to the state (the state shown in FIGS. 1 and 2) in which the first and second syringes 510A and 510B assume the priming orientation with the through holes 512 of the first and second syringes 510A and 510B positioned upper than the injector head body 100, and a state (the state shown in FIGS. 3 and 4) in which the first and second syringes 510A and 510B assume the contrast agent injectable orientation with the through holes 512 of the first and second syringes 510A and 510B positioned lower than the injector head body 100.

In the priming orientation shown in FIGS. 1 and 2, when viewed from the direction perpendicular to and parallel to the rotation axis AL, the central axis line SL of the first syringe 510A intersects the rotation axis AL on the side of through hole 512 of the first syringe 510A. In the contrast agent injectable orientation shown in FIGS. 3 and 4, the first syringe 510A is attached to injector head body 100 such that, when viewed from the direction perpendicular to and parallel to the rotation axis AL, the central axis line SL of the first syringe 510A intersects the rotation axis AL on the side of injector head body 100.

In the priming orientation shown in FIGS. 1 and 2, when viewed from the direction perpendicular to and parallel to the rotation axis AL, the central axis line SL of the second syringe 510B intersects the rotation axis AL on the side of injector head body 100 of the second syringe 510B. In the contrast agent injectable orientation shown in FIGS. 3 and 4, the second syringe 510B is attached to injector head body 100 such that, when viewed from the direction perpendicular to and parallel to the rotation axis AL, the central axis line SL of the second syringe 510B intersects the rotation axis AL on the side of through hole 512 of the second syringe 510B.

Consequently, even when injector head body 100 rotates between the "priming orientation" shown in FIGS. 1 and 2 and the "contrast agent injectable orientation" shown in FIGS. 3 and 4, coupling tube 12 extending from first flow path switching device 600 coupled to the first and second syringes 510A and 510B moves only around rotation axis AL.

As a result, interference between coupling tube 12 coupled to injector head 1 with rotation mechanism in accordance with the present embodiment and other devices becomes less likely. Therefore, ample margin for the tube length becomes unnecessary. Further, the burden on the engineer paying attention to avoid contact between the tube and other devices can be alleviated.

Though double-syringe type injector head 1 with rotation mechanism having two syringes has been described, the number of syringes is not limited to two, and the invention is applicable to a single-syringe type injector head with rotation mechanism using either one of the syringes.

Though a syringe having through hole 512 eccentric to central axis line CL is used as syringe 510, a syringe having through hole 512 provided on the central axis line CL may be used.

(Contrast Agent Injection Line L1000)

Next, a contrast agent injection line L1000 to the patient using injector head 1 with rotation mechanism having the structure above will be described with reference to FIG. 7. To the first and second syringes 510A and 510B attached to injector head body 100, first flow path switching device 600 is coupled. Details of first flow path switching device 600 will be described later.

Contrast agent injection line L1000 can be divided to a multi-use section S1 used for a plurality of patients, and one-time use sections S2 and S3 used only for one patient.

The multi-use section S1 will be described. Multi-use section S1 is shown surrounded by dotted lines in the figure. Multi-use section S1 has first flow path switching device 600. To first flow path switching device 600, a seventh tube 15 is coupled, and to the seventh tube 15, a contrast agent bag 16 is coupled. To first flow path switching device 600, coupling tube 12 leading to the patient is coupled. At the tip end of coupling tube 12, a connector 13 is connected.

The one-time use section S2 will be described. One-time use section S2 is shown surrounded by dotted lines in the figure. One-time use section S2 has a main tube 17 having a connector 14 connected to one end and a connector 20 connected to the other end. Connector 14 is connected to connector 13 of coupling tube 12.

Main tube 17 has a branch tube 17a. At the tip end of branch tube 17a, a connector 25 is connected. Opening/closing of main tube 17 and branch tube 17a is controlled by a second flow path switching device 800. Second flow path switching device 800 has fixed valve elements 801 and 802 and a change-over valve element 803, and change-over valve element 803 is controlled to move in the direction of an arrow RA10 in the figure. By fixed valve element 801 and change-over valve element 803, opening/closing of main tube 17 is controlled, and by fixed valve element 802 and change-over valve element 803, opening/closing of branch tube 17a is controlled.

Connector 25 of branch tube 17a is coupled to a connector 26 provided on a normal saline tube 19. Normal saline tube 19 has the other end coupled to a saline bag 21. A blood pressure transducer 300, a roller pump 400, and a third air sensor AS3 are provided on normal saline tube 19.

The one-time use section S3 will be described. One-time use section S3 is shown surrounded by dotted lines in the figure. One-time use section S3 has a tube 22 having one end connected to a connector 24 and the other end connected to a connector 23. To connector 24, connector 20 of main tube 17 is coupled. To connector 23, a catheter inserted to a blood vessel of a patient is coupled.

Blood pressure of a patient is measured using normal saline, with main tube 17 closed by fixed valve element 801 and change-over valve element 803 and branch tube 17a communicated with saline bag 21. For the measurement of blood pressure, electric signals from blood pressure transducer 300 are used.

When contrast agent is to be introduced from injector head 1 with rotation mechanism to the patient, branch tube 17a is closed and the main tube 17 is opened by fixed valve element 802 and change-over valve element 803.

(First Flow Path Switching Device 600 and Priming Operation)

Next, referring to FIGS. 8 to 15, first flow path switching device 600 and the priming operation will be described. FIGS. 8 to 15 show the first to ninth steps of the priming process in injector head 1 with rotation mechanism. In the present embodiment, the priming operation as described below is automatically executed by a control device mounted inside injector head body 100.

First flow path switching device 600 should be represented by dotted lines as the main components are positioned on the other side of the device. For convenience of description, however, the device is shown by solid lines in FIGS. 8 to 15.

Figure 8:
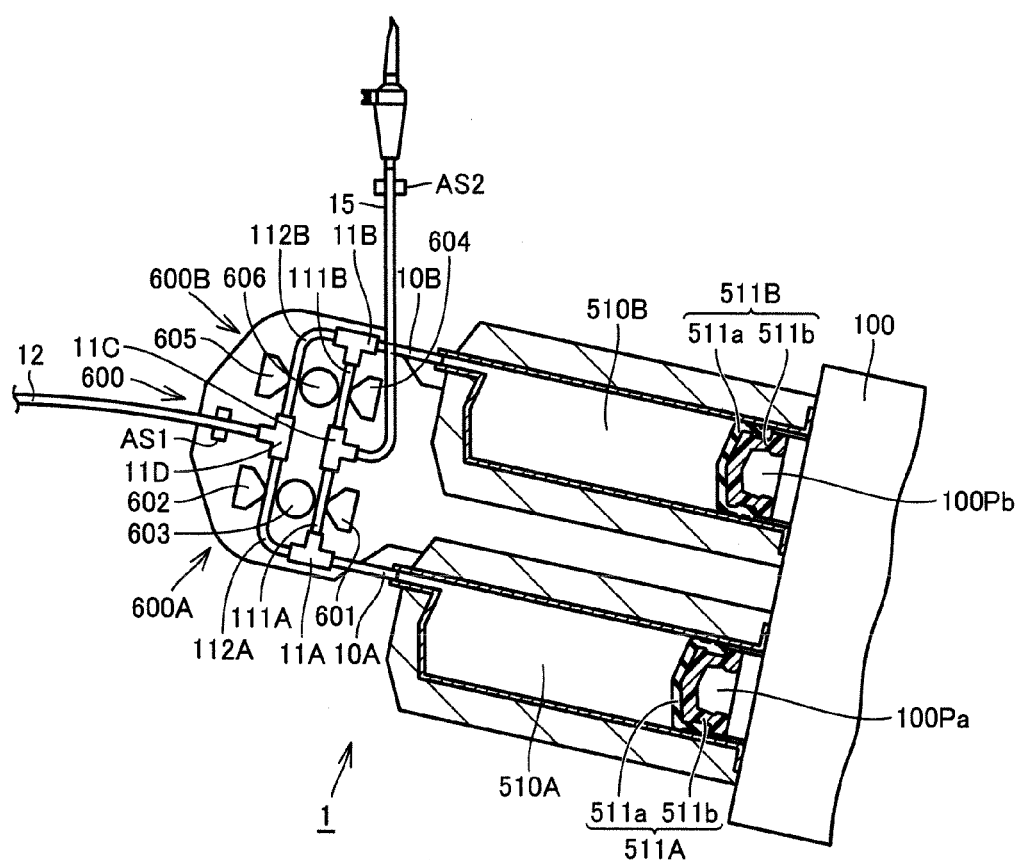
FIG. 8 shows a first step of the priming process for the injector head with rotation mechanism in accordance with an embodiment.

Referring to FIG. 8, in the priming operation, the first and second syringes 510A and 510B are positioned such that through holes 512 face upward, as described with reference to FIGS. 1 and 2.

To injector head body 100, first syringe 510A having contrast agent Z filled therein and second syringe 510B having contrast agent Z filled therein are mounted. A piston 511A coupled to a first plunger 100Pa is provided inside first syringe 510A, and a second piston 511B coupled to a second plunger 100Pb is provided inside second syringe 510B.

One end of a first tube 10A is coupled to the first syringe 510A. The other end of first tube 10A is coupled to a first T-shaped tube 11A. To the first T-shaped tube 11A, one end of a third tube 111A and one end of a fifth tube 112A are coupled, respectively.

One end of a second tube 10B is coupled to the second syringe 510B. The other end of second tube 10B is coupled to a second T-shape tube 11B. To the second T-shaped tube 11B, one end of a fourth tube 111B and one end of a sixth tube 112B are coupled, respectively.

The third and fourth tubes 111A and 111B each have the other end coupled to a third T-shaped tube 11C. Further, to the third T-shaped tube 11C, the seventh tube 15, having the other end coupled to a contrast agent bag 16, is coupled.

The fifth and sixth tubes 112A and 112B each have the other end coupled to a fourth T-shaped tube 11D. To the fourth T-shaped tube 11D, coupling tube 12, having the other end coupled to connector 13, is coupled.

A first air sensor AS1 detecting entrance of air to the tube is provided on coupling tube 12, and a second air sensor AS2 detecting entrance of air to the tube is provided on the seventh tube 15.

(First Flow Path Switching Device 600)

First flow path switching device 600 is provided for switching opening/closing of the third tube 111A and opening/closing of the fifth tube 112A. First flow path switching device 600 has a first flow path switching mechanism 600A and a second flow path switching mechanism 600B.

First flow path switching mechanism 600A is provided for switching between the third and fifth tubes 111A and 112A arranged parallel to each other, and the second flow path switching mechanism 600B is provided for switching between the fourth and sixth tubes 111B and 112B arranged parallel to each other.

The first flow path switching mechanism 600A has a first change-over valve element 603 provided between the third and fifth tubes 111A and 112A and movable in a direction intersecting the direction of extension of the tubes. Further, first flow path switching mechanism 600A has first and second fixed valve elements 601 and 602 at positions opposite to the first change-over valve element 603 with respective tubes interposed.

Similarly, the second flow path switching mechanism 600B has a second change-over valve element 606 provided between the fourth and sixth tubes 111B and 112B and movable in a direction intersecting the direction of extension of the tubes. Further, the second flow path switching mechanism 600B has third and fourth fixed valve elements 604 and 605 at positions opposite to the second change-over valve element 606 with respective tubes interposed.

(Priming Operation: First Step)

Next, the priming operation using the first flow path switching device 600 having the structure above will be described with reference to FIGS. 8 to 15. Injector head 1 with rotation mechanism in accordance with the present embodiment is set to the priming orientation in which the side of first through hole 512A of first syringe 510A is positioned upper than the side of injector head body 100 (first plunger (100Pa)) and the side of second through hole 512B of second syringe 510B is positioned upper than the side of injector head body 100 (second plunger (100Pb)), by rotating injector head body 100 about the rotation axis AL as the center of rotation, as shown in FIGS. 1 and 2. The priming operation refers to the operation of expelling air from the first and second syringes 510A and 510B and from various tubes.

Referring to FIG. 8, in a state where contrast agent bag 16 is not coupled to the seventh tube 15, the first piston 511A in the first syringe 510A and the second piston 511B in the second syringe 510B, not filled with contrast agent but empty, are set to the rearmost positions. Further, the first change-over valve element 603 of the first flow path switching mechanism 600A and the second change-over valve element 606 are positioned at neutral positions, and the third, fifth, fourth and sixth tubes 111A, 112A, 111B and 112B are opened. Here, the first air sensor does not output any signal.

(Second Step)

Figure 9:
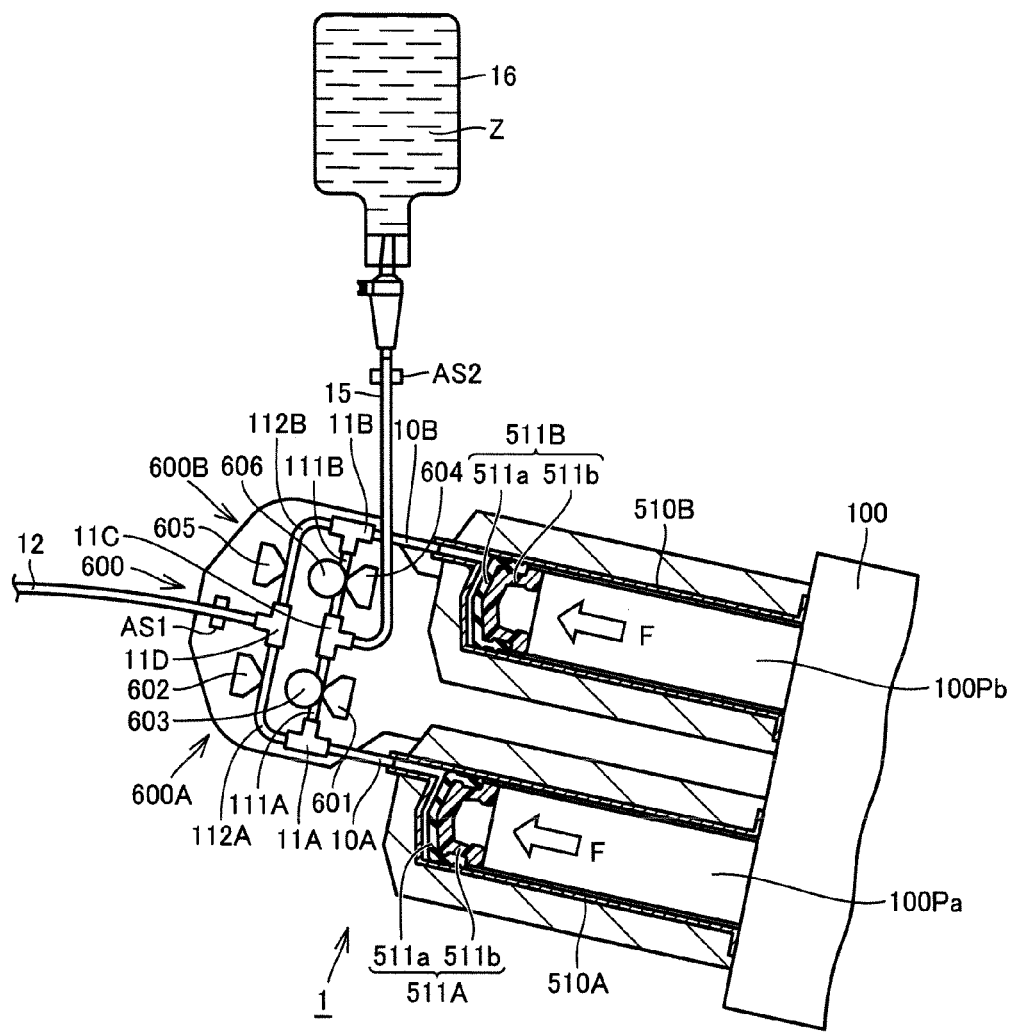
FIG. 9 shows a second step of the priming process for the injector head with rotation mechanism in accordance with an embodiment.

Next, as shown in FIG. 9, the first change-over valve element 603 of first flow path switching mechanism 600A is moved to the side of the first fixed valve element 601, to close the third tube 111A. Further, the second change-over valve element 606 of the second flow path switching mechanism 600B is moved to the side of the third fixed valve element 604, to close the fourth tube 111B. Next, contrast agent bag 16 is coupled to the seventh tube 15, and the first piston 111A in the first syringe 510A and the second piston 511B in the second syringe 510B are moved to the foremost position (in the direction indicated by an arrow F in FIG. 9), to discharge air in the first and second syringes 510A and 510B to the outside.

(Third Step)

Figure 10:
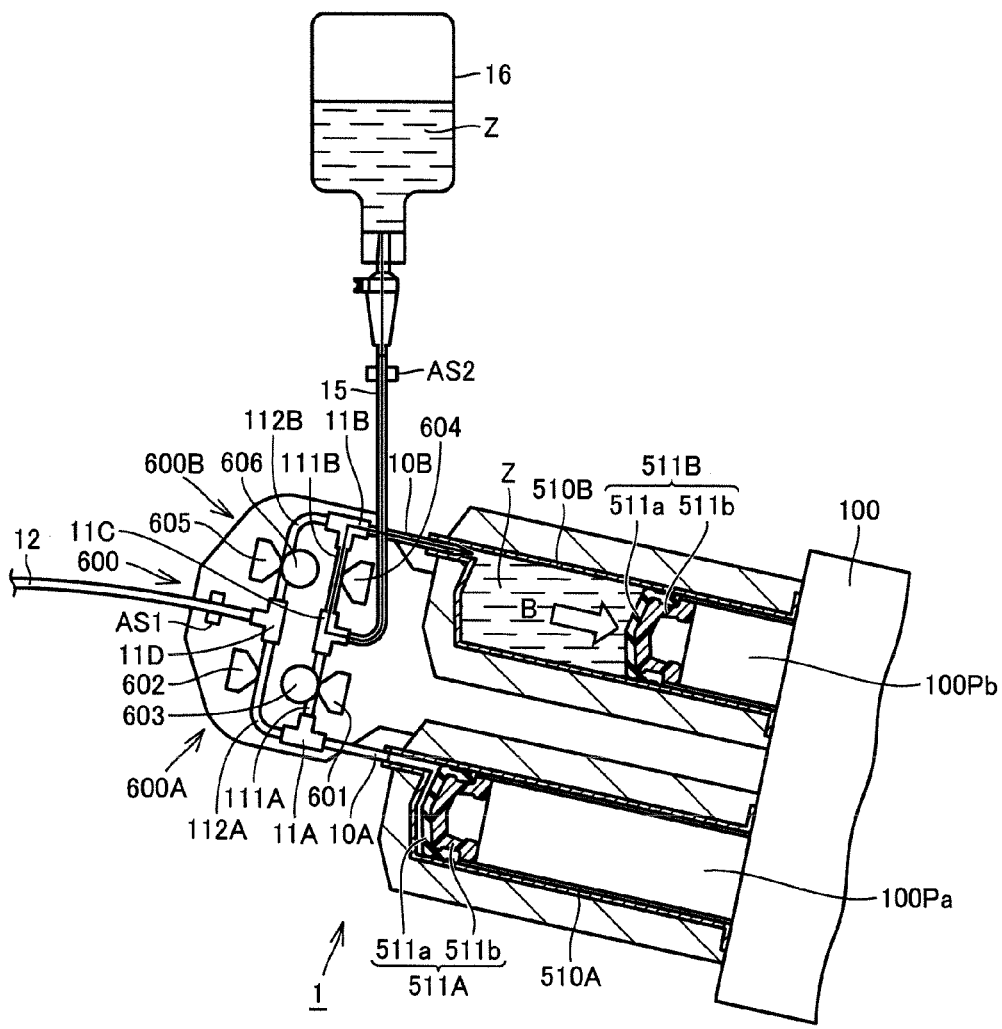
FIG. 10 shows a third step of the priming process for the injector head with rotation mechanism in accordance with an embodiment.

Next, as shown in FIG. 10, the second change-over valve element 606 of the second flow path changing mechanism 600B is moved to the side of the fourth fixed valve element 605, to open the fourth tube 111B and close the sixth tube 112B. Thereafter, the second piston 511B in the second syringe 510B is moved backward (in the direction of the arrow B in the figure), and contrast agent Z is introduced from contrast agent bag 16 to the second syringe 510B.

(Fourth Step)

Figure 11:
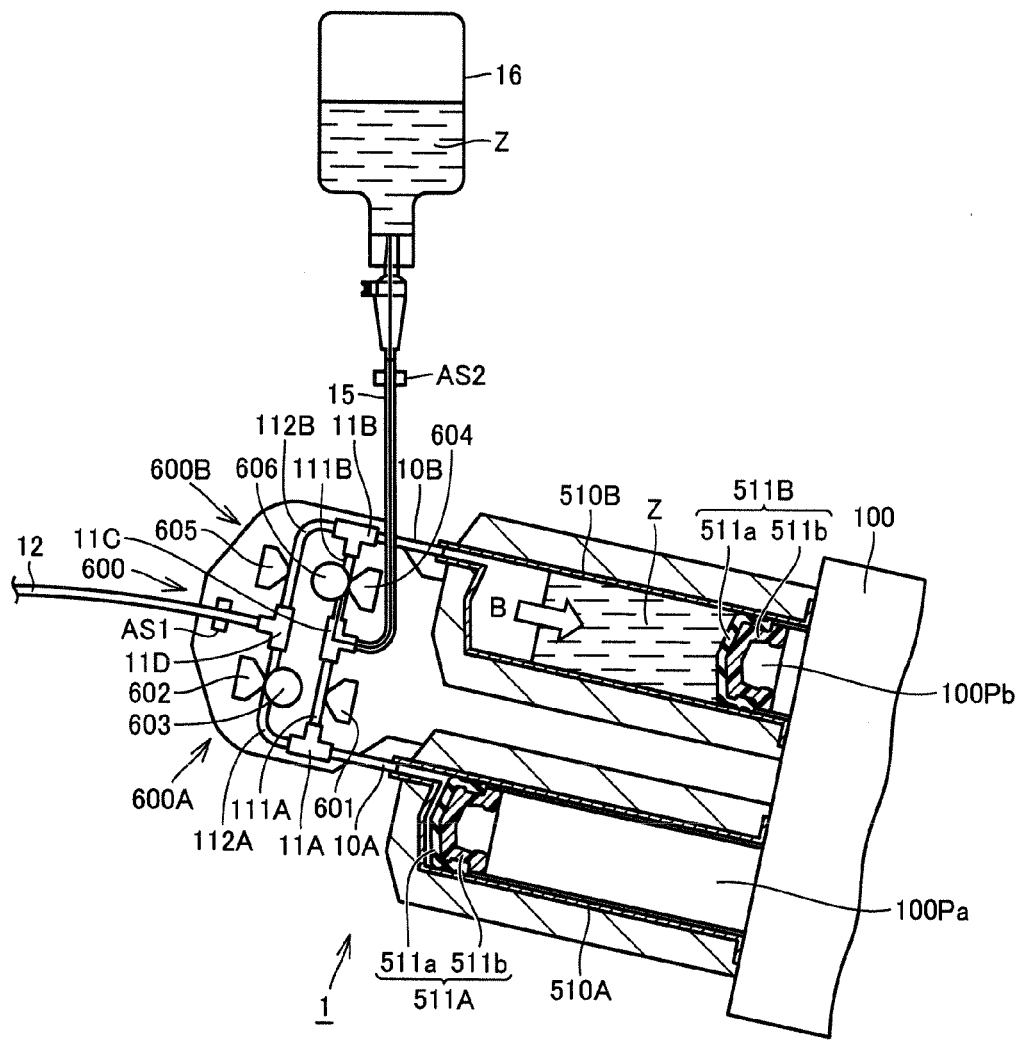
FIG. 11 shows a fourth step of the priming process for the injector head with rotation mechanism in accordance with an embodiment.

Next, referring to FIG. 11, after a prescribed amount of contrast agent Z is introduced to the second syringe 510B, the second change-over valve element 606 is moved to the side of the third fixed valve element 604 to close the fourth tube 111B, and the first change-over valve element 603 is moved to the side of the second fixed valve element 602 to close the fifth tube 112A. Thereafter, the second piston 511B in the second syringe 510B is moved backward (in the direction of the arrow B in the figure), to introduce a prescribed amount of air to the second syringe 510B.

(Fifth Step)

Figure 12:
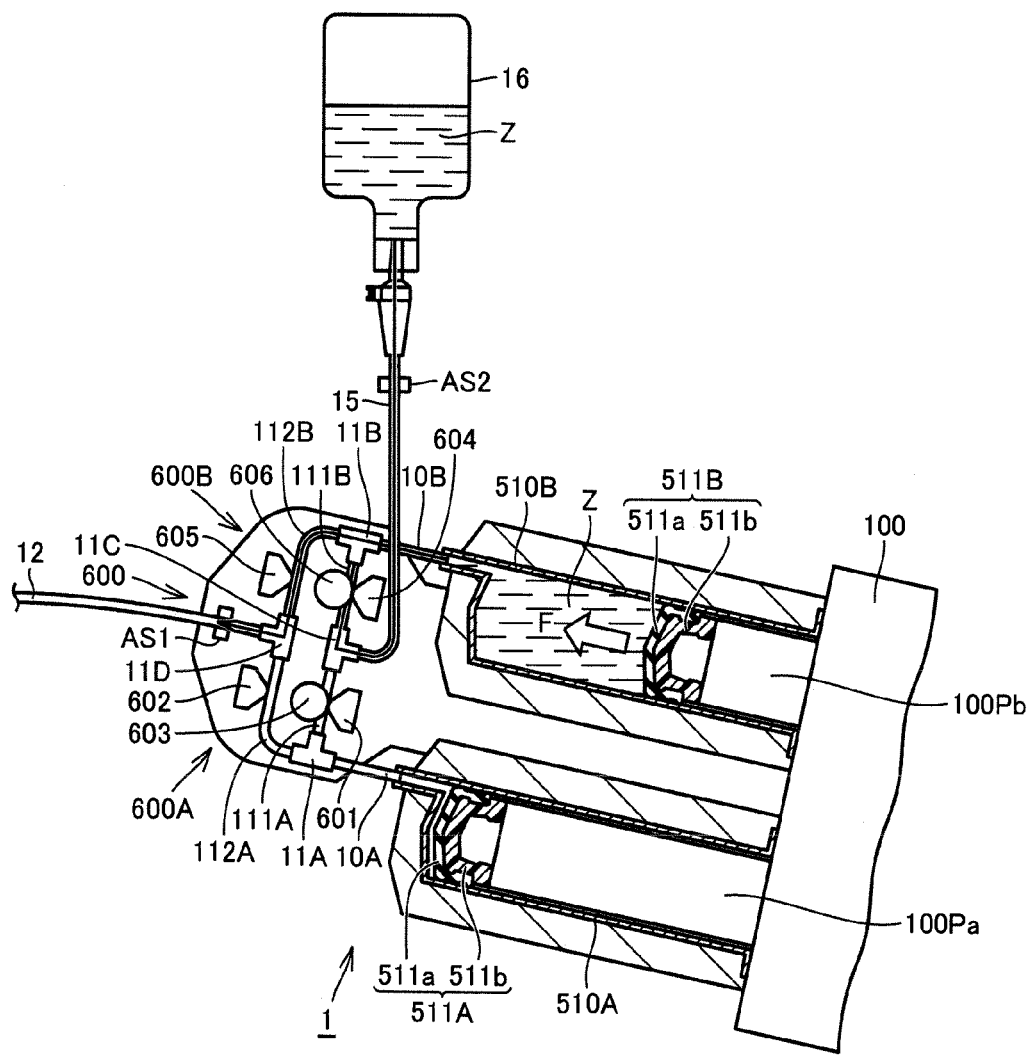
FIG. 12 shows a fifth step of the priming process for the injector head with rotation mechanism in accordance with an embodiment.

Next, referring to FIG. 12, the first change-over valve element 603 is moved to the side of the first fixed valve element 601, to close the third tube 111A. Thereafter, the second piston 511B in the second syringe 510B is moved forward (in the direction of the arrow F in FIG. 12) until passage of the contrast agent is detected by the first air sensor AS1.

(Sixth Step)

Figure 13:
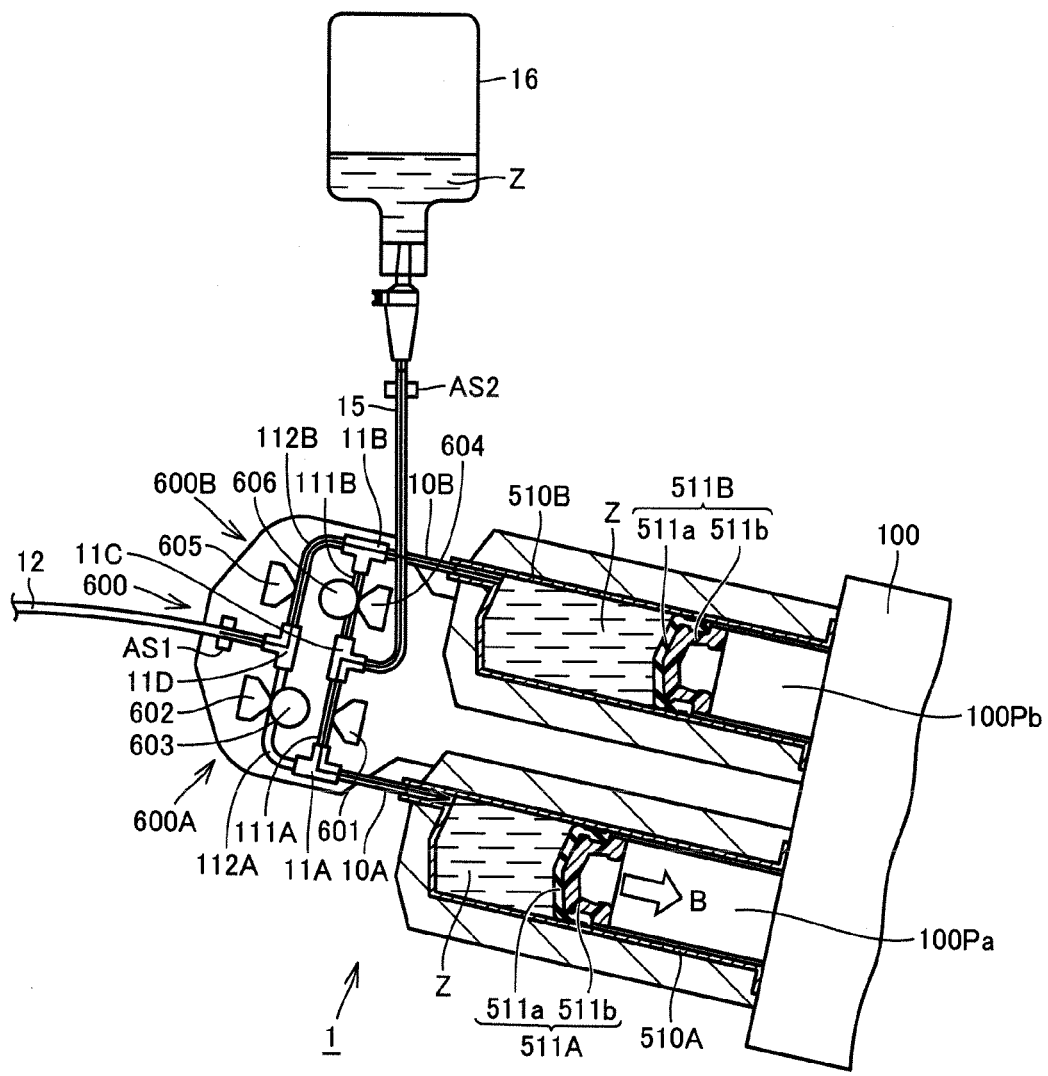
FIG. 13 shows a sixth step of the priming process for the injector head with rotation mechanism in accordance with an embodiment.

Next, referring to FIG. 13, the first change-over valve element 603 of the first flow path changing mechanism 600A is moved to the side of the second fixed valve element 602 to open the third tube 111A and to close the fifth tube 112A. Thereafter, the first piston 511A in the first syringe 510A is moved backward (in the direction of the arrow B in FIG. 13), and the contrast agent Z is introduced from contrast agent bag 16 to the first syringe 510A.

(Seventh Step)

Figure 14:
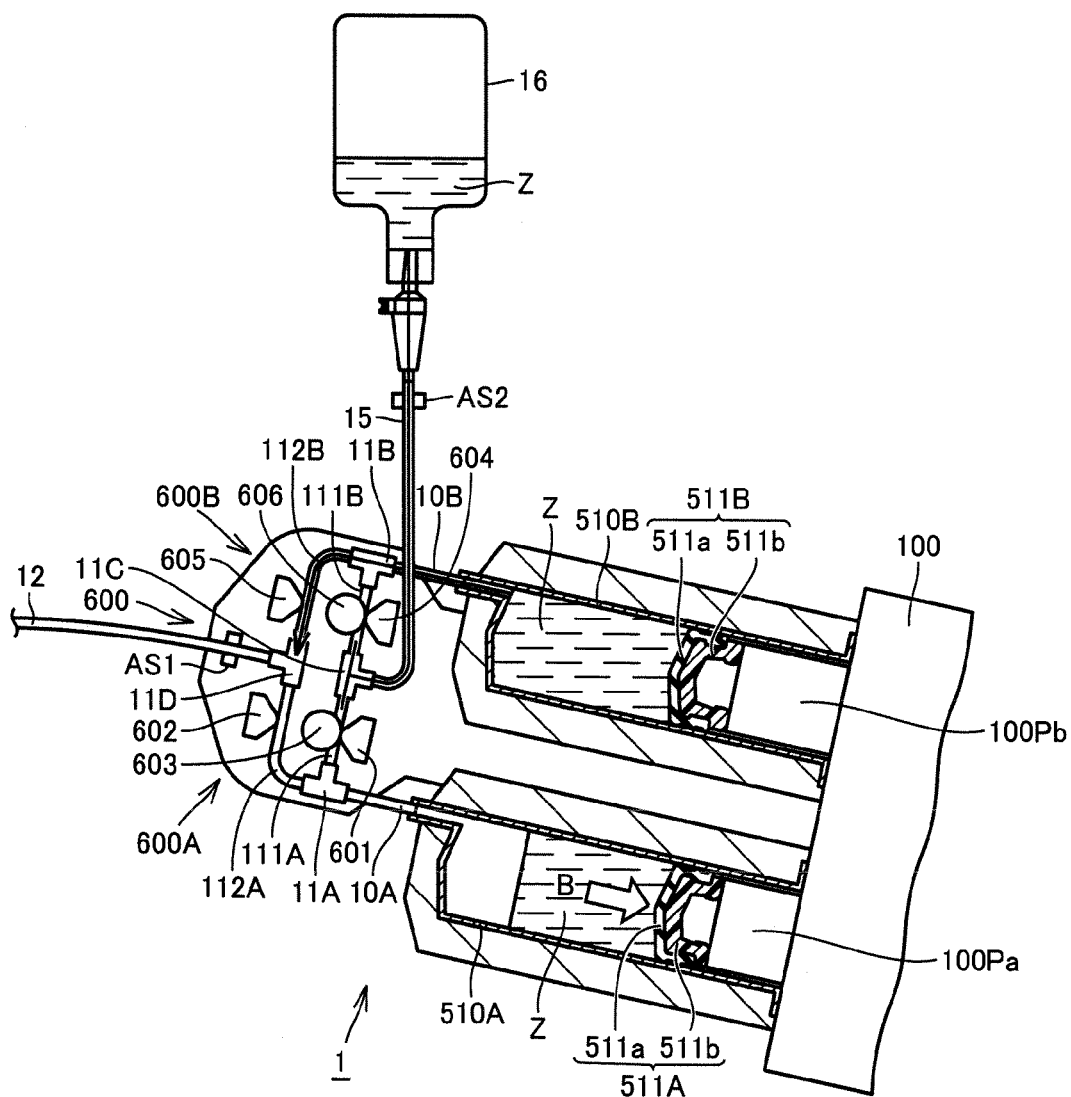
FIG. 14 shows a seventh step of the priming process for the injector head with rotation mechanism in accordance with an embodiment.

Next, referring to FIG. 14, after a prescribed amount of contrast agent Z is introduced to the first syringe 510A, the first change-over valve element 603 is moved to the side of the first fixed valve element 601 to close the third tube 111A. Thereafter, the first piston 511A in the second syringe 510A is moved backward (in the direction of the arrow B in FIG. 14), to introduce a prescribed amount of air to the first syringe 510A.

(Eighth Step)

Figure 15:
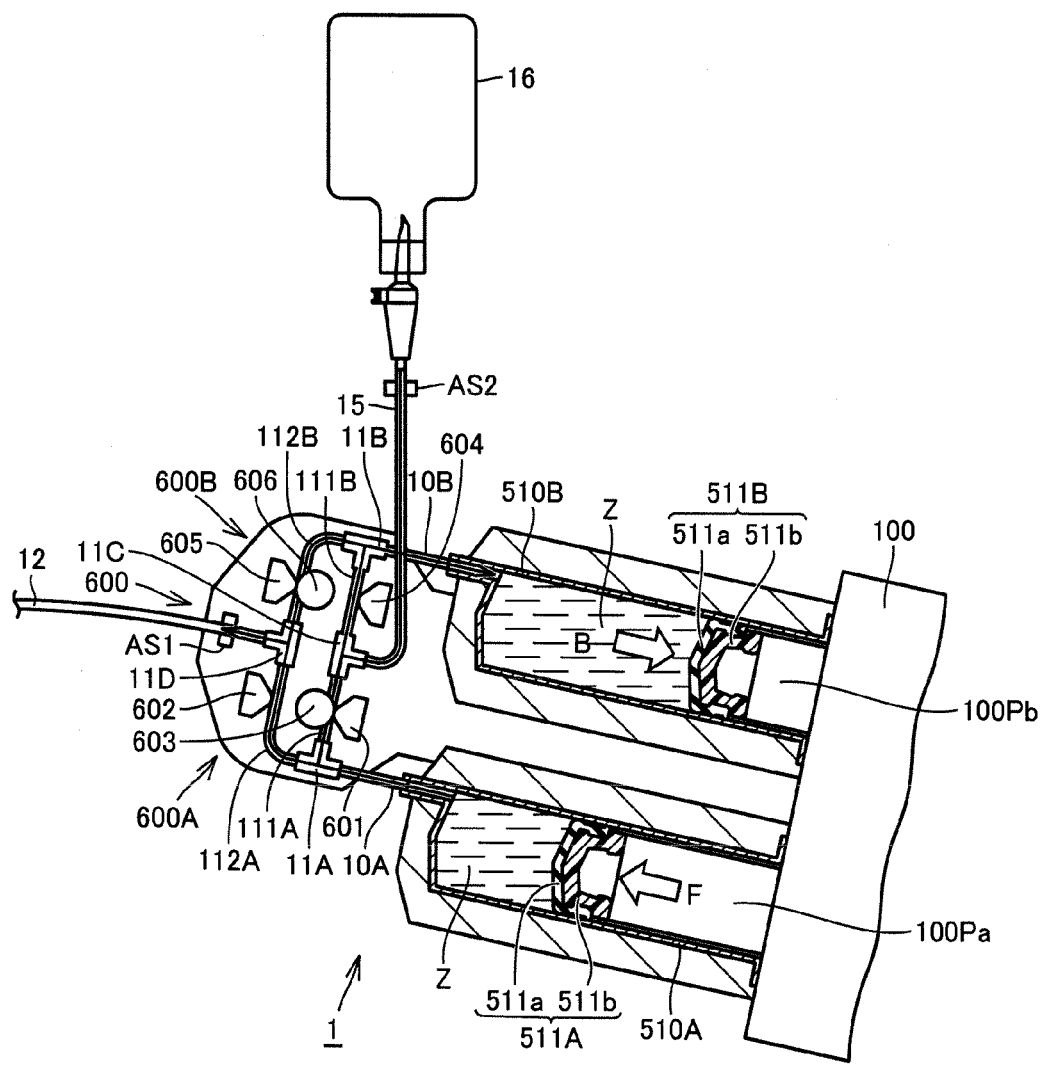
FIG. 15 shows an eighth step of the priming process for the injector head with rotation mechanism in accordance with an embodiment.

Next, referring to FIG. 15, the second change-over valve element 606 is moved to the side of the fourth fixed valve element 605 to close the sixth tube 112B. In this state, the first piston 511A in the first syringe 510A is moved forward (in the direction of the arrow F in FIG. 15) until passage of the contrast agent is detected by the first air sensor AS1 and the second piston 511B in the second syringe 510B is moved backward (in the direction of the arrow B in FIG. 15) until the passage of contrast agent is no longer detected by the second air sensor AS2.

By the operations described above, the priming operation of the first and second syringes 510A and 510B using the first flow path changing device 600 is completed, and air is expelled from the first and second syringes 510A and 510B as well as from the first, second, third, fourth, fifth and sixth tubes 10A, 10B, 111A, 111B, 112A and 112B.

In the priming process described above, presence/absence of the contrast agent Z in the tube is detected by using first and second air sensors AS1 and AS2. If capacity of the syringes, length of each tube, capacity of each tube and the like are known in advance, the priming process may be executed without using the first and second air sensors AS1 and AS2.

(Contrast Agent Injecting Operation)

Next, the operation of injecting contrast agent using the first flow path switching device 600 having the structure as above will be described with reference to FIGS. 16 to 18. After the completion of the above-described priming operation, injector head 1 with rotation mechanism is set to the contrast agent injectable orientation in which the first through hole 512A of the first syringe 510A is positioned lower than injector head body 100 (the first plunger (100Pa)) and the second through hole 512B of the second syringe 510B is positioned lower than injector head body 100 (the second plunger (100Pb)), by rotating injector head body 100 about the rotation axis AL as the center of rotation, as shown in FIGS. 3 and 4.

Figure 16:
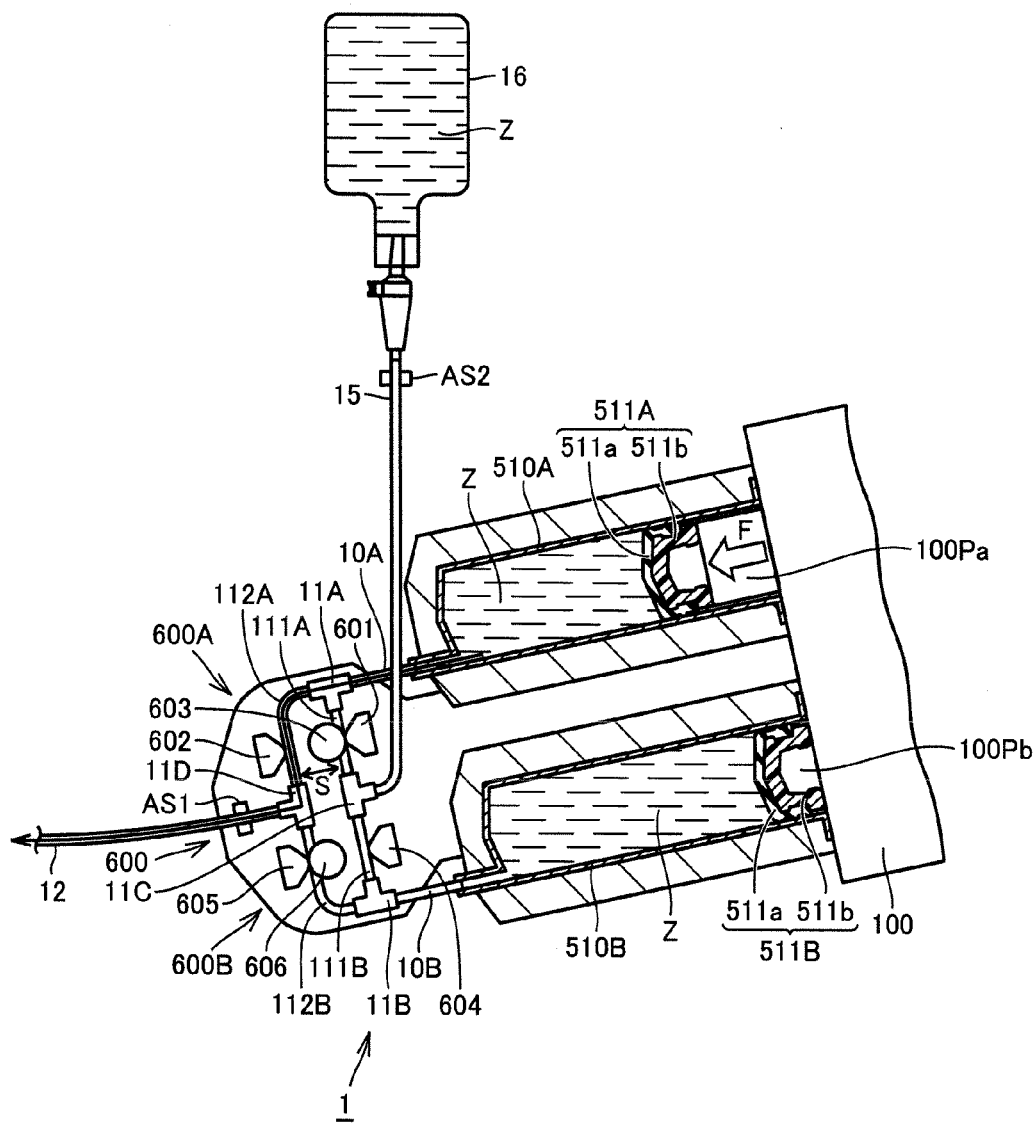
FIG. 16 is a first illustration showing the process of contrast agent injection and suction by the injector head with rotation mechanism in accordance with an embodiment.

Referring to FIG. 16, the first change-over valve element 603 of the first flow path switching mechanism 600A is moved to the side of the first fixed valve element 601, to close the third tube 111A. The second change-over valve element 606 of the second flow path switching mechanism 600B is moved to the side of the fourth fixed valve element 605, to close the sixth tube 112B.

Consequently, the first syringe 510A comes to be communicated with coupling tube 12. By the driving of injector head body 100, the first plunger 100Pa is moved forward (in the direction of the arrow F in FIG. 16), and the contrast agent inside is fed through contrast agent injection line L1000 to the patient.

Figure 17:
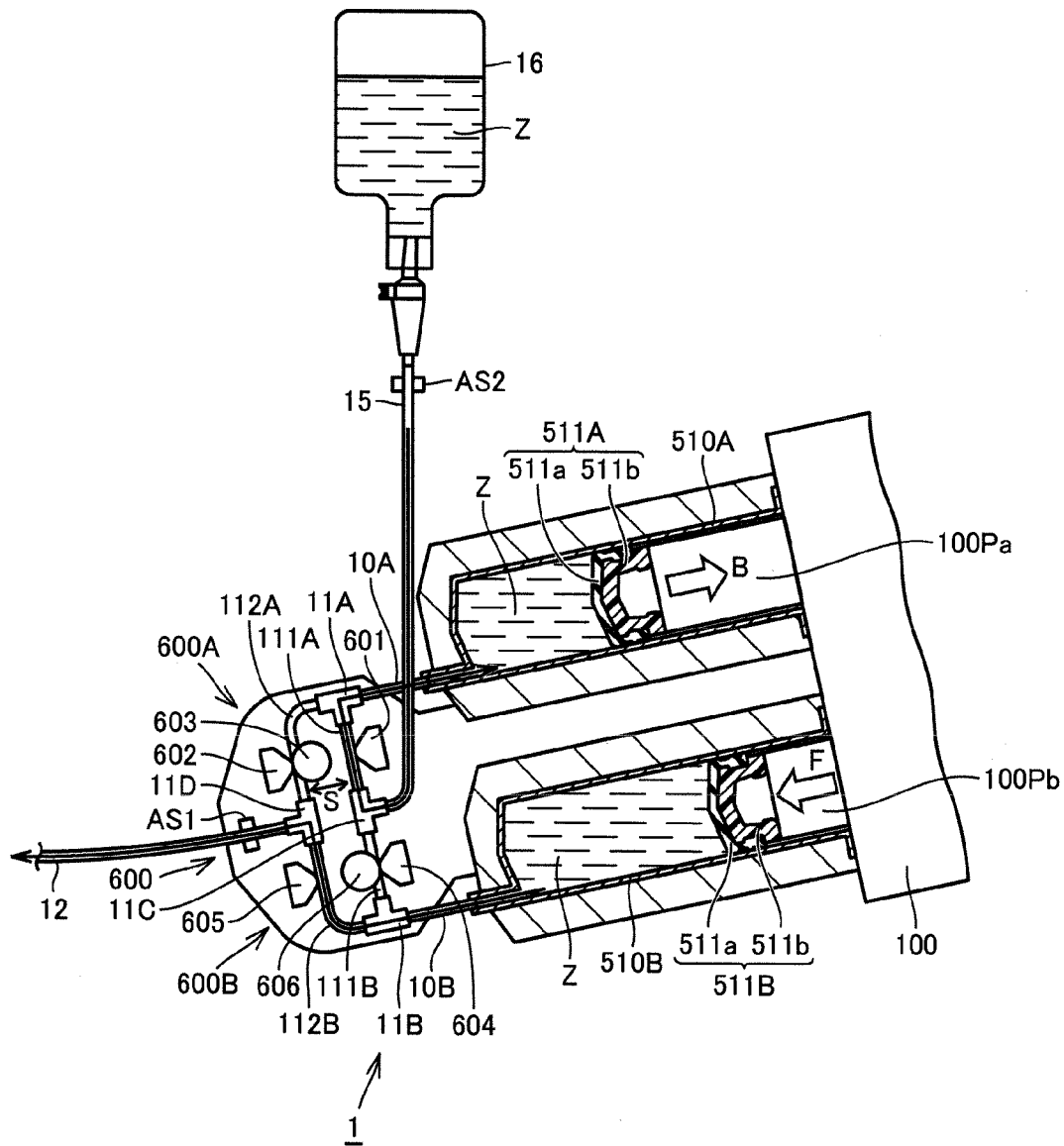
FIG. 17 is a second illustration showing the process of contrast agent injection and suction by the injector head with rotation mechanism in accordance with an embodiment.
Figure 18:
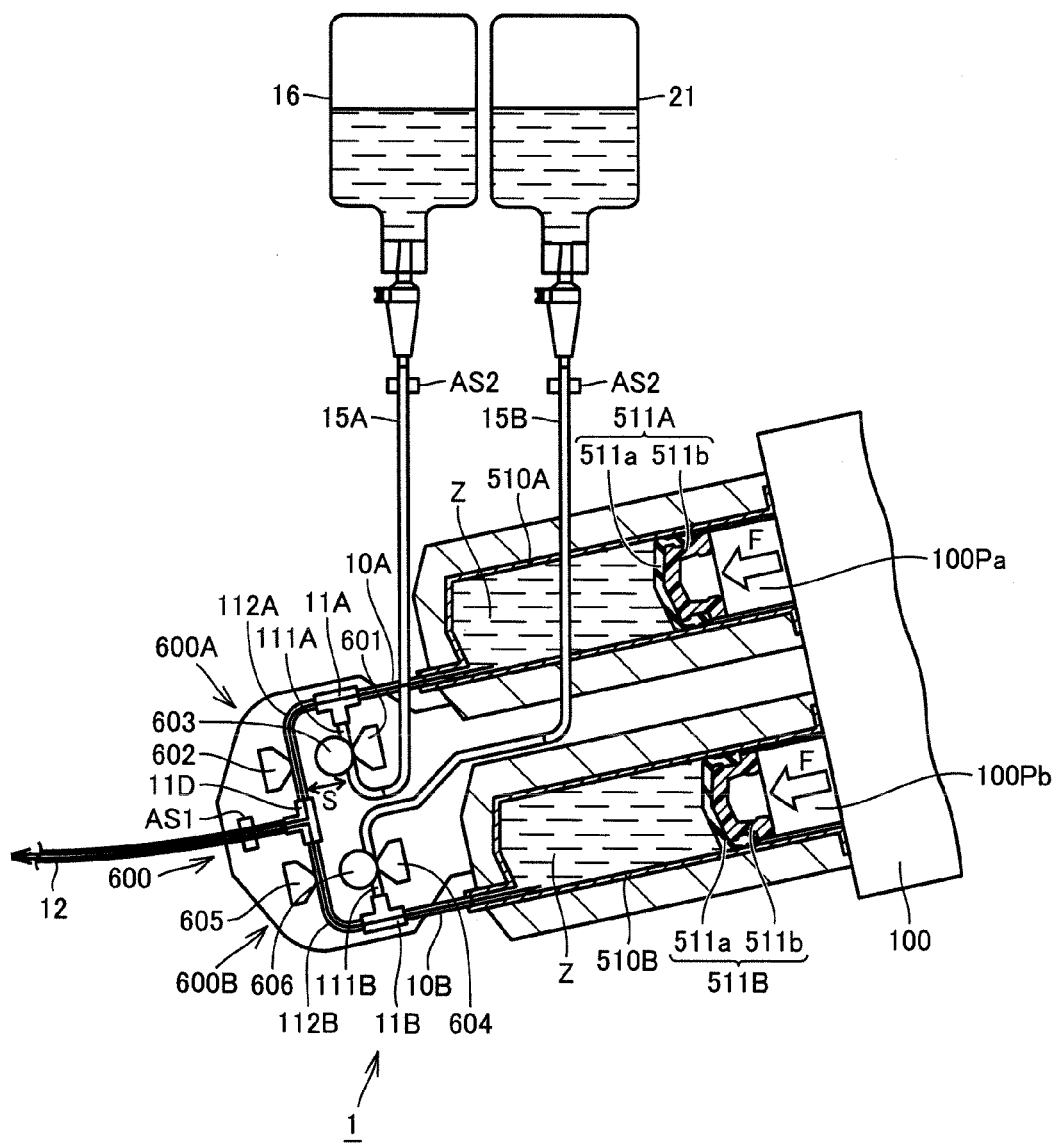
FIG. 18 is a third illustration showing the process of contrast agent injection and suction by the injector head with rotation mechanism in accordance with an embodiment.

Next, referring to FIG. 17, when the contrast agent in the first syringe 510A is used up, switching between the first and second flow path switching mechanisms 600A and 600B is realized by the first flow path switching device 600. Specifically, the first change-over valve element 603 of the first flow path switching mechanism 600A is moved to the side of the second fixed valve element 602 to close the fifth tube 112A. Further, the second change-over valve element 606 of the second flow path switching mechanism 600B is moved to the side of the third fixed valve element 604 to close the fourth tube 111B.

Consequently, the first syringe 510A is communicated with contrast agent bag 16, and the second syringe 510B is communicated with coupling tube 12. Thus, by simultaneously moving backward the first plunger 100Pa of the first syringe 510A (in the direction of the arrow B in FIG. 17) and moving forward the second plunger 100Pb of the second syringe 510B (in the direction of the arrow F in FIG. 17), suction of contrast agent Z to the first syringe 510A and injection of contrast agent Z from the second syringe 510B can be attained simultaneously. If it is unnecessary to perform the contrast agent suction process to the first syringe 510A, backward movement of the first plunger 100Pa is unnecessary.

By simultaneously moving forward the first plunger 100Pa of the first syringe 510A and moving backward the second plunger 100Pb of the second syringe 510B in the similar manner, it is also possible to simultaneously attain the process of injecting the contrast agent from the first syringe 510A and the contrast agent suction process to the second syringe 510B.

(Mixed Injection)

Referring to FIG. 14, by directly coupling the third tube 111A to the eighth tube 15A coupled to contrast agent bag 16 and directly coupling the fourth tube 111B to the ninth tube 15B coupled to saline bag 21, without using the third T-shaped tube 11C, mixed injection becomes possible.

Specifically, the first change-over valve element 603 of the first flow path switching mechanism 600A is moved to the side of the first fixed valve element 601 to close the third tube 111A. Further, the second change-over valve element 606 of the second flow path switching mechanism 600B is moved to the side of the third fixed valve element 604, to close the fourth tube 111B. Consequently, the first and second syringes 510A and 510B are communicated with coupling tube 12, so that mixed injection of contrast agent Z and normal saline to the patient becomes possible.

Further, by switching the first change-over valve element 603 of the first flow path switching mechanism 600A and the second change-over valve element 606 of the second flow path switching mechanism 600B to close the fifth and fourth tubes 112A and 111B, suction of the contrast agent to first syringe 510A and suction of normal saline to the second syringe 510B can be attained simultaneously.

(Positions of Engineer and Doctor)

Figure 19:
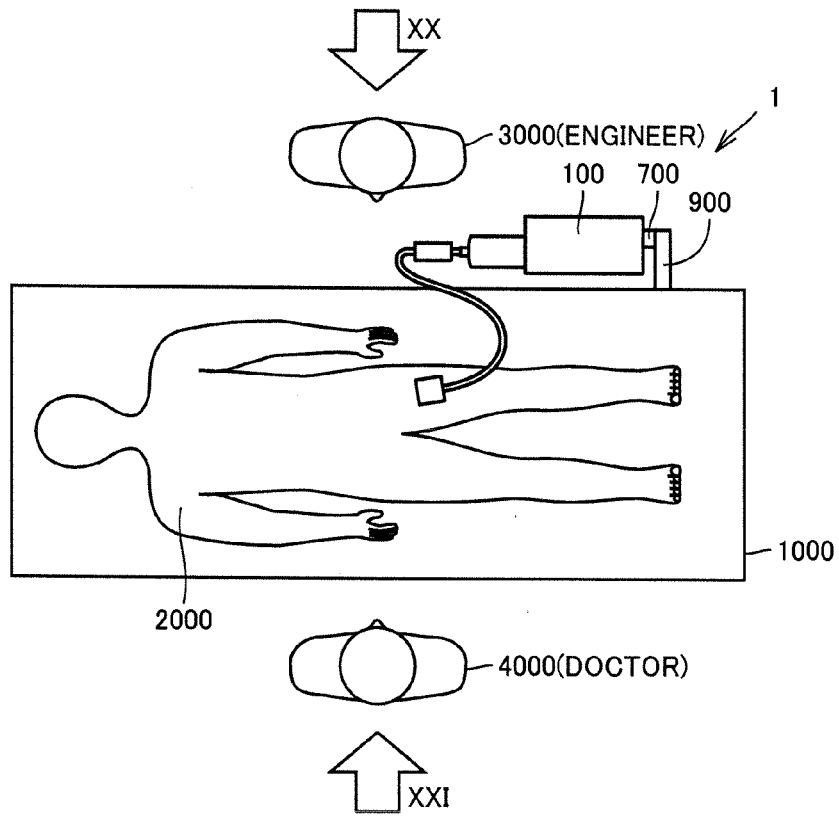
FIG. 19 is a plan view showing the state of contrast agent injection to a patient using the injector head with rotation mechanism in accordance with an embodiment.

Next, positions of the engineer and the doctor when a test is conducted using injector head 1 with rotation mechanism in accordance with the present embodiment will be described with reference to FIGS. 19 to 21. FIG. 19 is a plan view showing the state of contrast agent injection to a patient 2000 using injector head 1 with rotation mechanism, FIG. 20 shows injector head 1 with rotation mechanism in the priming orientation, viewed from the side of the engineer shown in FIG. 19, and FIG. 21 shows injector head 1 with rotation mechanism in the contrast agent injectable orientation, viewed from the side of the doctor shown in FIG. 19.

Figure 20:
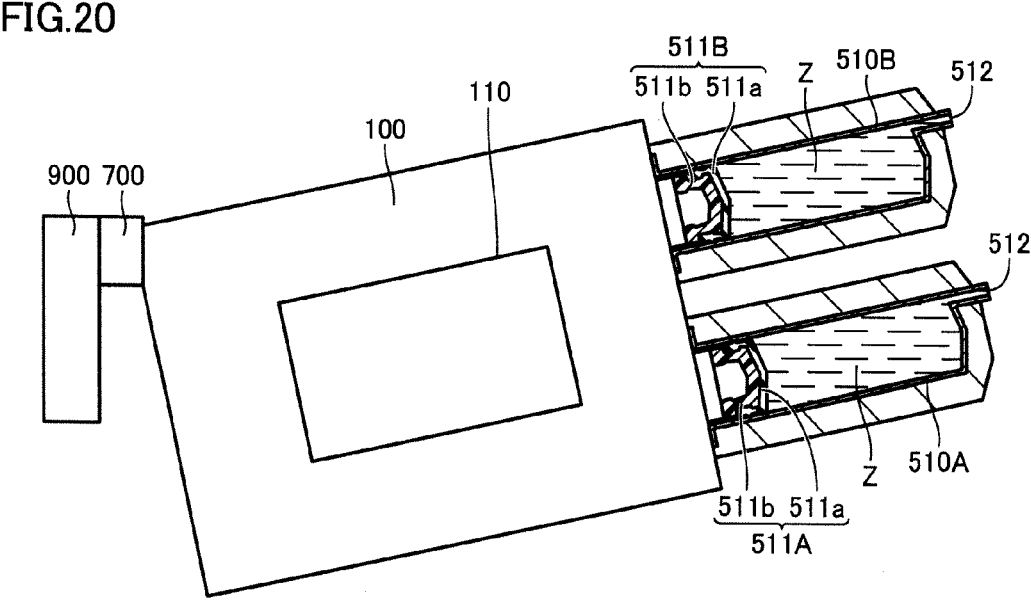
FIG. 20 shows the injector head with rotation mechanism in accordance with an embodiment, in the priming orientation, viewed from the side of the engineer shown in FIG. 19.

Referring to FIGS. 19 and 20, the above-described priming operation is carried out by an engineer 3000. Therefore, when injector head 1 with rotation mechanism in accordance with the present embodiment is placed on the left side of a patient 2000 on a bed 1000, it follows that the engineer 3000 also stands on the left side of patient 2000, that is, on the same side of injector head 1 with rotation mechanism.

In injector head body 100, an orientation sensor (not shown) for detecting the orientation is provided, and operation information in accordance with the priming operation is displayed on an operation monitor 110 implemented by a touch-panel.

Figure 21:
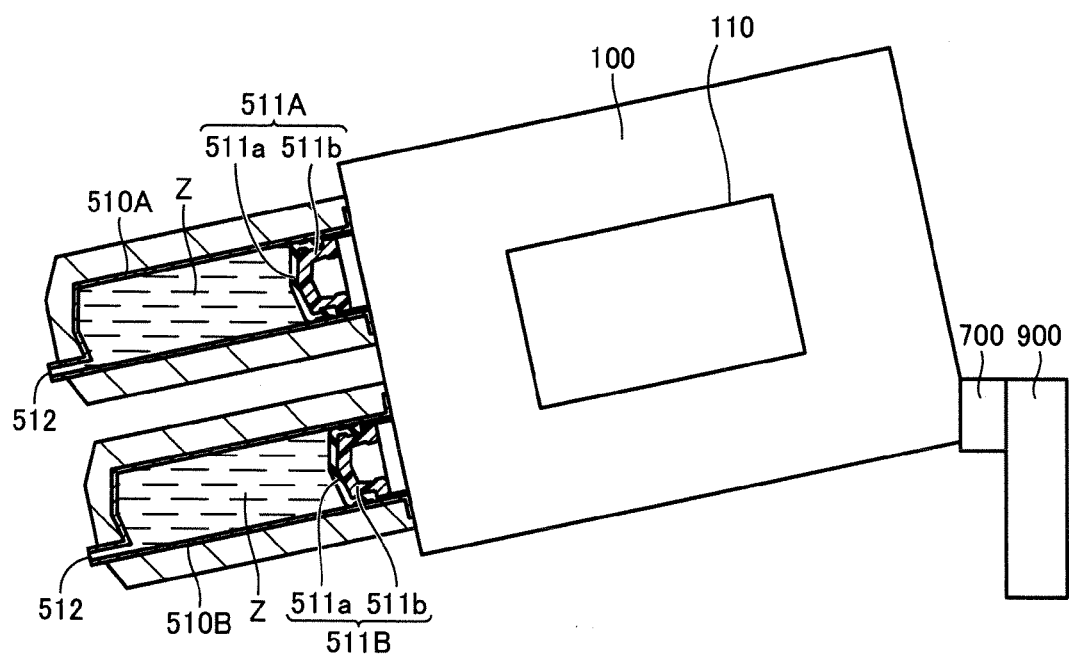
FIG. 21 shows the injector head with rotation mechanism in accordance with an embodiment, in the contrast agent injectable orientation, viewed from the side of the doctor shown in FIG. 19.

Referring to FIGS. 19 and 21, the contrast agent injecting operation with injector head 1 with rotation mechanism rotated is carried out by a doctor 4000. Here, it follows that doctor 4000 stands opposite to engineer 3000, on the other side of bed 1000.

Because of the rotation, operation monitor 110 comes to face doctor 4000, and the orientation is detected by the orientation sensor provided inside and the operation instruction in accordance with the contrast agent injecting operation is displayed on operation monitor 110.

In this manner, when injector head 1 with rotation mechanism in accordance with the present embodiment is used, the test can be conducted smooth even when engineer 3000 and doctor 4000 stand on opposite sides of bed 1000.

(Alternative Example of Second Flow Path Switching Device 800A)

Figure 22:
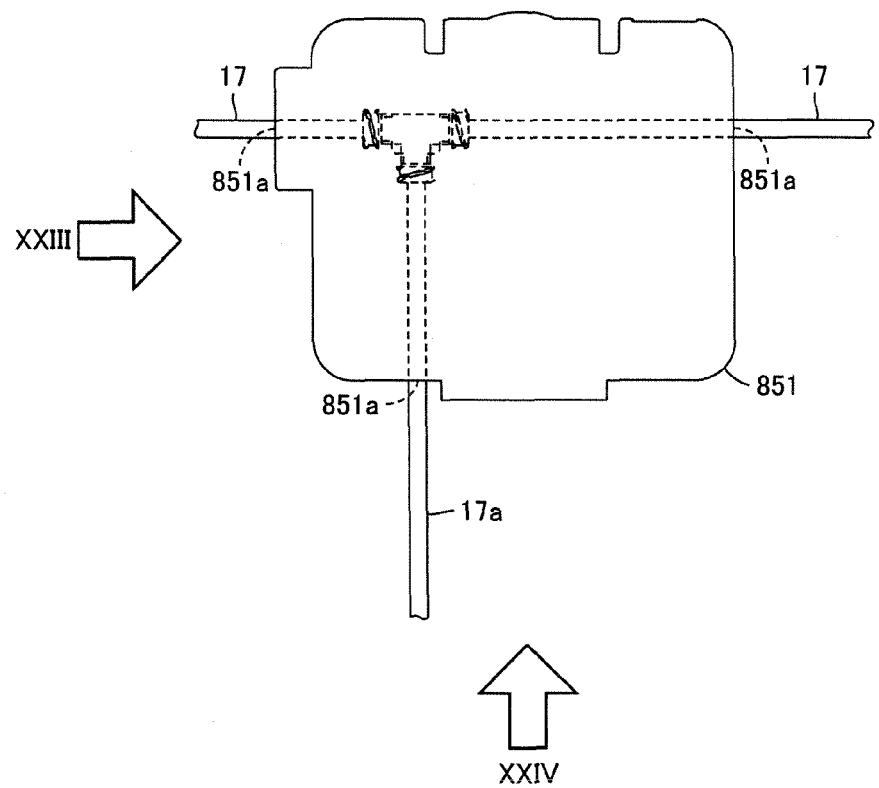
FIG. 22 shows a flow path switching device of an alternative example, used in the injector head with rotation mechanism in accordance with an embodiment.

Next, an alternative example of the second flow path switching device 800A, corresponding to the second flow path switching device 800 shown in FIG. 7, will be described with reference to FIGS. 22 to 29. FIG. 22 shows the second flow path switching device 800A, FIG. 23 is a cross-sectional view from a direction of an arrow XXIII of FIG. 22, FIG. 24 is a cross-sectional view from a direction of an arrow XXIV of FIG. 22, FIG. 25 shows an internal structure of the second flow path switching device 800A, and FIGS. 26 to 29 are first to fourth illustrations showing state of operations of the second flow path switching device 800A.

Figure 23:
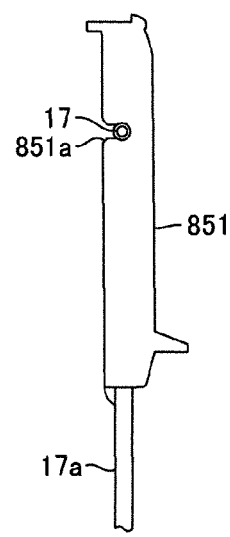
FIG. 23 is a cross-sectional view from a direction of an arrow XXIII of FIG. 22.
Figure 24:
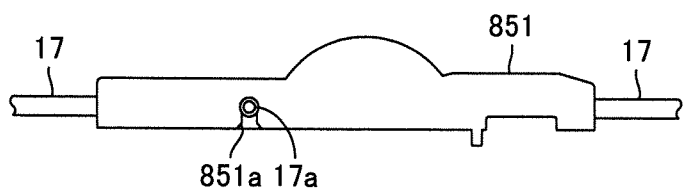
FIG. 24 is a cross-sectional view from a direction of an arrow XXIV of FIG. 22.

Referring to FIGS. 22 to 24, the second flow path switching device 800A has a cover 851. On three of the four side surfaces of cover 851 (left side surface, right side surface and lower side surface in the figure), tube receiving recesses 851a are provided. Main tube 17 and branch tube 17a are fixed on tube receiving recesses 851a.

Figure 25:
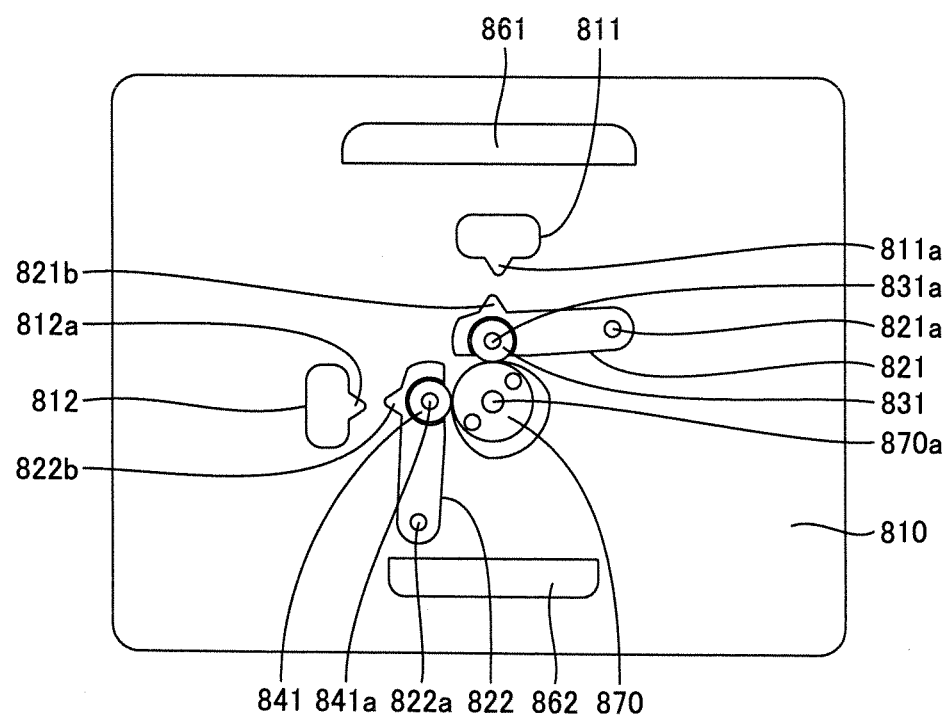
FIG. 25 shows an internal structure of a second flow path switching device of the alternative example, used in the injector head with rotation mechanism in accordance with an embodiment.

Referring to FIG. 25, the second flow path switching device 800A has a main body 810. On main body 810, cover 851 with main tube 17 and branch tube 17a fixed, is detachably attached. It is noted that cover 851 is not shown in FIG. 25.

At upper and lower positions of main body 810, engaging pieces 861 and 862 are provided to detachably hold cover 851, pinching cover 851 both from the upper and lower sides.

At the central position of main body 810, a rotating cam 870 is provided, which rotates about a rotation shaft 870a as the center of rotation. On the outer circumferential surface of rotating cam 870, a cam face is formed, to control movement of movable valve elements 821 and 822, which will be described later. Rotation of rotating cam 870 is controlled by a driving device (servo motor or the like) provided in main body 810.

A fixed valve element 811 is fixed on main body 810 at an upper side of rotating cam 870. Fixed valve element 811 has a fixed projection 811a protruding toward rotating cam 870. A movable valve element 821 is provided on main body 810 between rotating cam 870 and fixed valve element 811. At a position of movable valve element 821 opposite to fixed projection 811a, a movable projection 821b is provided.

At one end of movable valve element 821, a rotation shaft 821a is provided, and movable valve element 821 is fixed on main body 810 rotatable about rotation shaft 821a as the center. At the other end of movable valve element 821, a contact roller 831 rotatable about a rotation shaft 831a and in contact with rotating cam 870 is provided.

A fixed valve element 812 is fixed on main body 810 on the left side of rotating cam 870. Fixed valve element 812 has a fixed projection 812a protruding toward rotating cam 870. A movable valve element 822 is provided on main body 810 between rotating cam 870 and fixed valve element 812. At a position of movable valve element 822 opposite to fixed projection 812a, a movable projection 822b is provided.

At a lower end of movable valve element 822, a rotation shaft 822a is provided, and movable valve element 822 is fixed on main body 810 rotatable about rotation shaft 822a as the center. At the other end of movable valve element 822, a contact roller 841 rotatable about a rotation shaft 841a and in contact with rotating cam 870 is provided.

Next, the states of operation of the second flow path switching device 800A will be described with reference to FIGS. 26 to 29. Though main tube 17 and branch tube 17a are mounted on main body 810 fixed on cover 851, for convenience of description, cover 851 is not shown.

Figure 26:
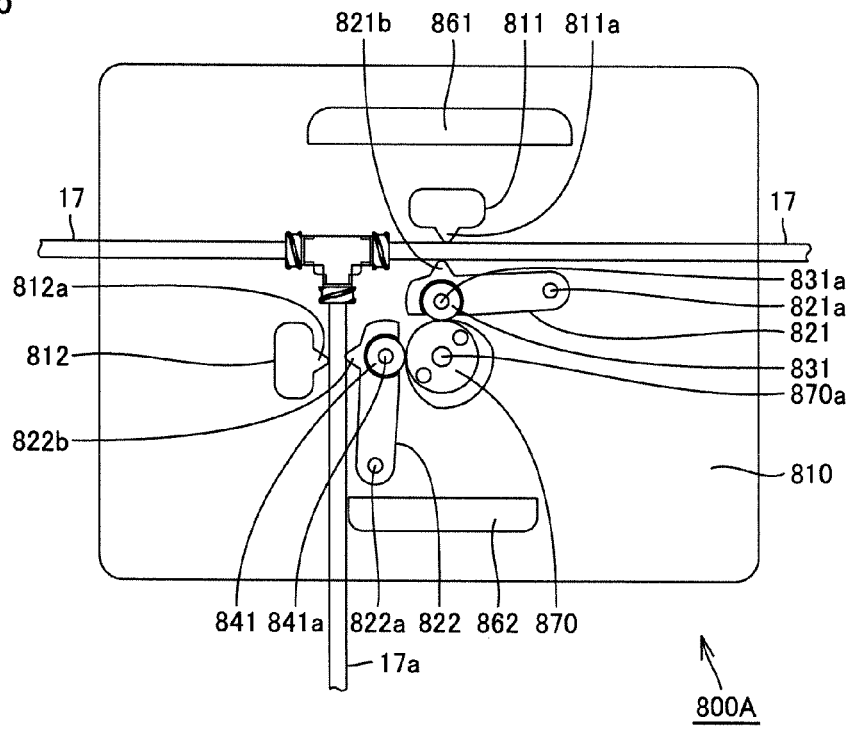
FIG. 26 is a first illustration showing a state of operation of the second flow path switching device of the alternative example, used in the injector head with rotation mechanism in accordance with an embodiment.

Referring to FIG. 26, rotating cam 870 is fixed at an initial state position. In this state, between fixed projection 811a and movable projection 821b, there is a space equal to or wider than the outer diameter of main tube 17. Similarly, between fixed projection 812a and movable projection 822b, there is a space equal to or wider than the outer diameter of branch tube 17a.

Figure 27:
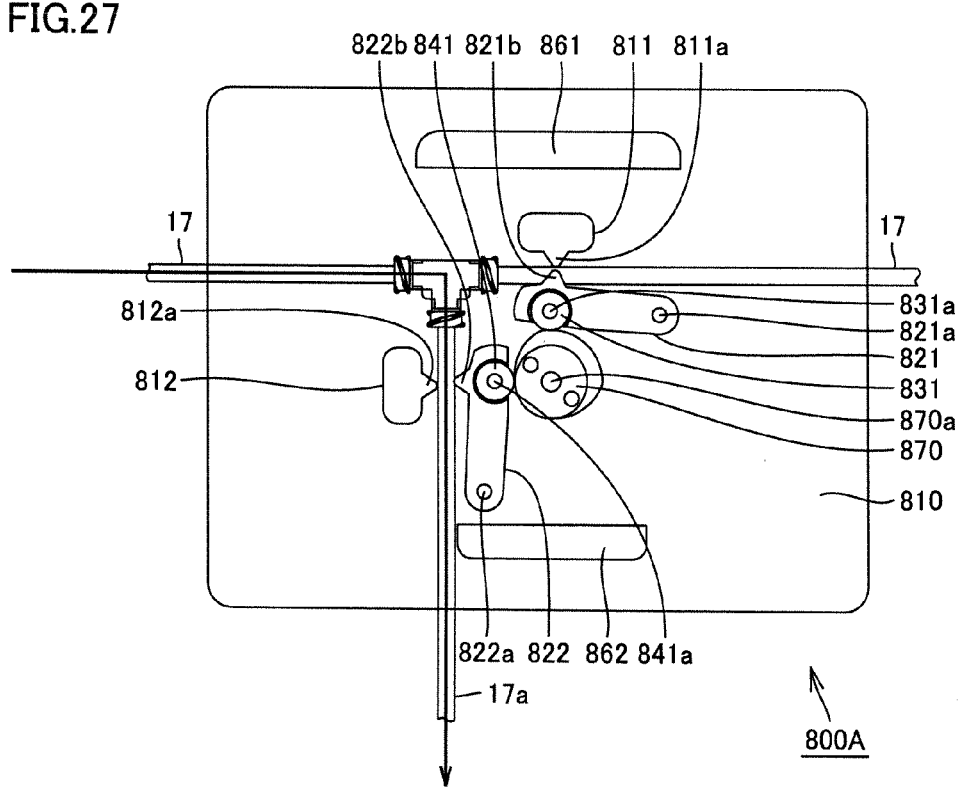
FIG. 27 is a second illustration showing a state of operation of the second flow path switching device of the alternative example, used in the injector head with rotation mechanism in accordance with an embodiment.

Referring to FIG. 27, rotating cam 870 is rotated counterclockwise by 90°. Thus, contact roller 831 is pushed upward by the cam face of rotating cam 870. As a result, main tube 17 is pinched between fixed projection 811a and movable projection 821b, and the tube path of main tube 17 is closed. At this time, branch tube 17a is open.

Figure 7:
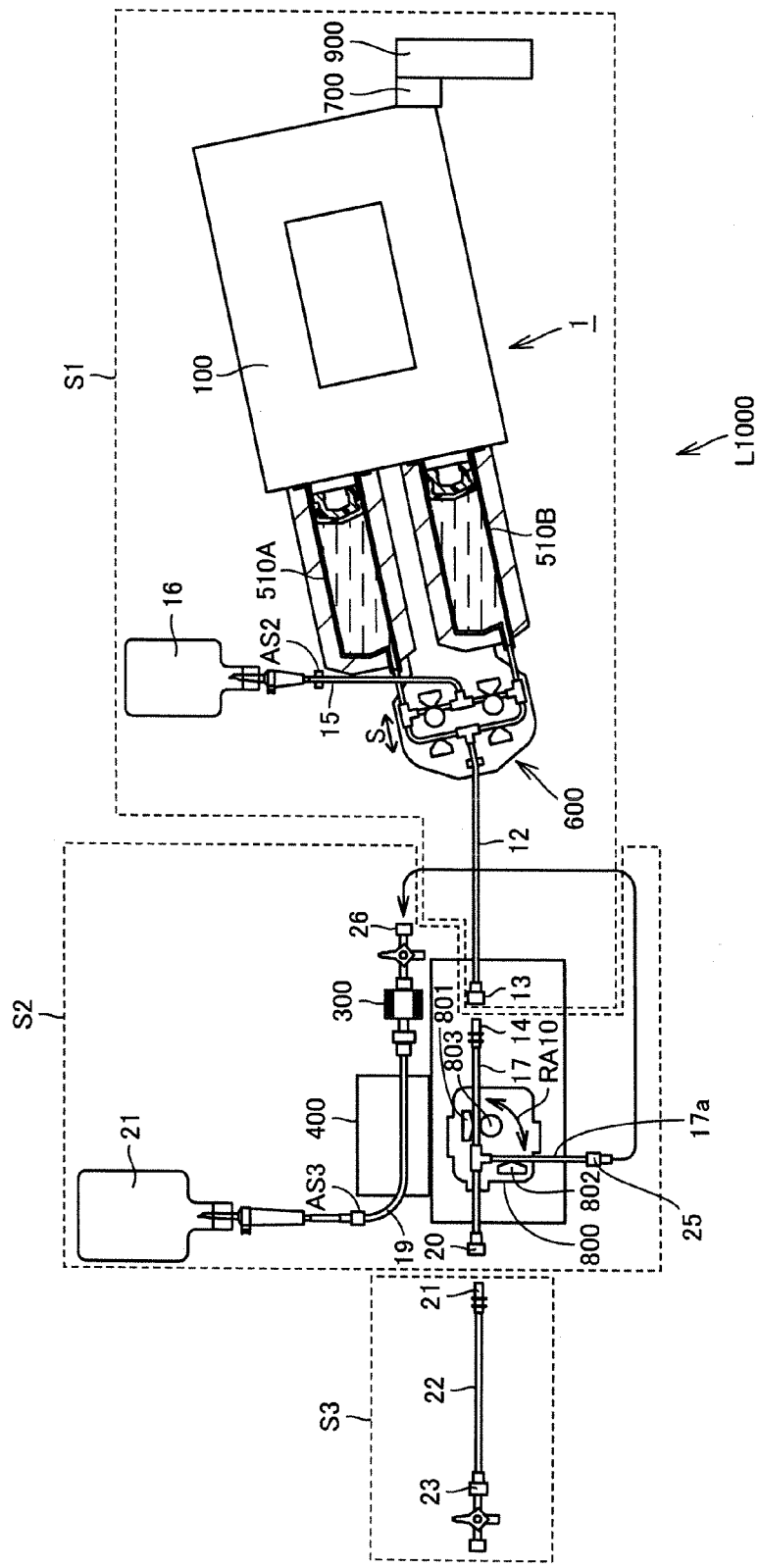
FIG. 7 shows a contrast agent introducing line to a patient, using the injector head with rotation mechanism in accordance with an embodiment.

This state corresponds to the state where tube 22 and blood pressure transducer 300 are communicated in FIG. 7, and it is possible to measure blood pressure of the patient (blood pressure measuring state).

Figure 28:
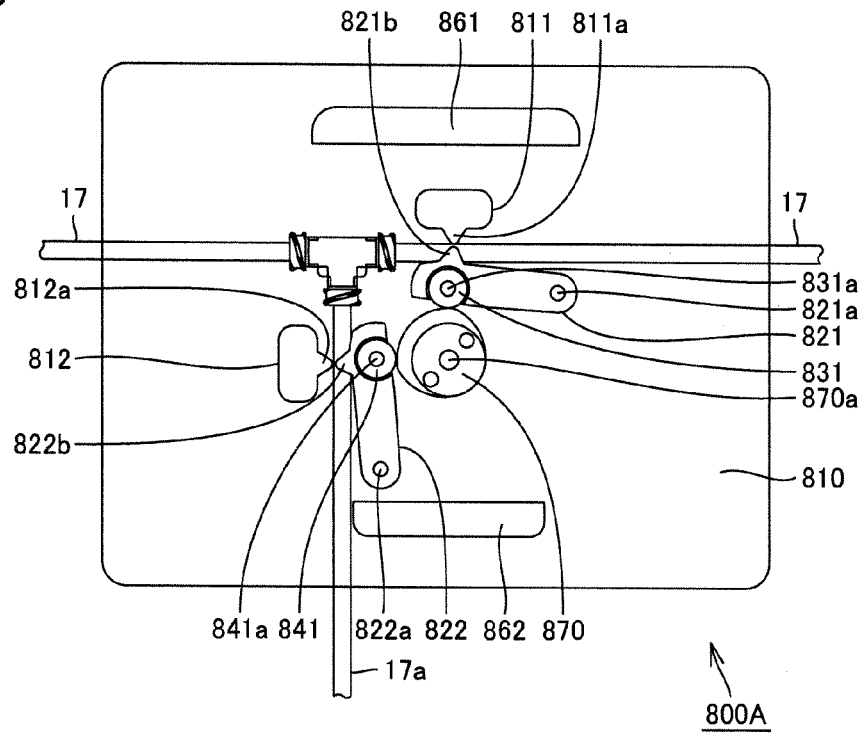
FIG. 28 is a third illustration showing a state of operation of the second flow path switching device of the alternative example, used in the injector head with rotation mechanism in accordance with an embodiment.

Referring to FIG. 28, rotating cam 870 is further rotated counterclockwise by 90°. Thus, while the state in which contact roller 831 is pushed upward by the cam face of rotating cam 870 is maintained, contact roller 841 is pushed to the left by the cam face of rotating cam 870. As a result, main tube is pinched between fixed projection 811a and movable projection 821b and tube path of main tube 17 is closed, and at the same time, branch tube 17a is pinched between fixed projection 812a and movable projection 822b, and the tube path of branch tube 17a is closed (closed state).

Figure 29:
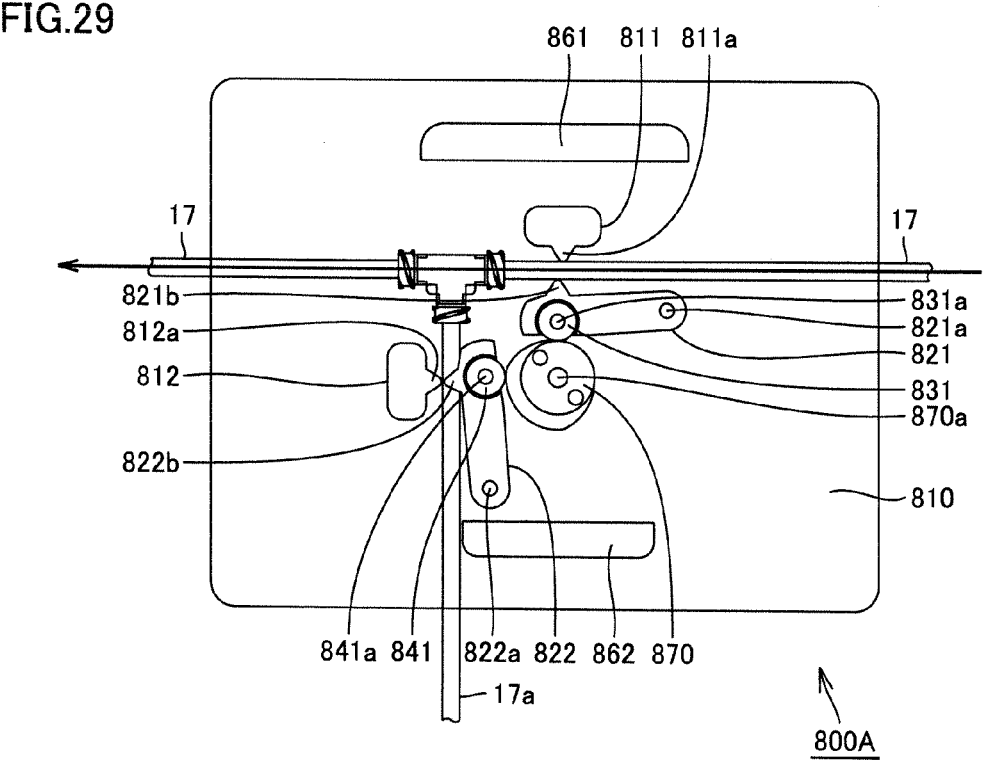
FIG. 29 is a fourth illustration showing a state of operation of the second flow path switching device of the alternative example, used in the injector head with rotation mechanism in accordance with an embodiment.

Referring to FIG. 29, rotating cam 870 is further rotated counterclockwise by 90°. Thus, pushing of contact roller 831 upward by the cam face of rotating cam 870 is cancelled, and main tube 17 is released. On the other hand, contact roller 841 is kept pushed to the left by the cam face of rotating cam 870, and tube path of main tube 17 is opened.

This state corresponds to the state in which tube 22 is communicated with injector head 1 with rotation mechanism in FIG. 7, and injection of contrast agent to the patient is possible (contrast agent injection state).

When rotating cam 870 is further rotated counterclockwise by 90°, the state of FIG. 26 is resumed. It is noted that for the switching between the blood pressure measuring state shown in FIG. 27 and the contrast agent injection state shown in FIG. 29, rotation of rotating cam 870 is controlled such that the closed state shown in FIG. 28 is interposed. The time required for rotation of rotating cam 870 for switching between the blood pressure measuring state and the contrast agent injecting state is about 0.3 seconds.

In injector head 1 with rotating mechanism in accordance with the present embodiment described above, the first and second syringes 510A and 510B are arranged along the up/down (vertical) direction with respect to injector head body 100 in the priming orientation and the contrast agent injectable orientation.

Figure 30:
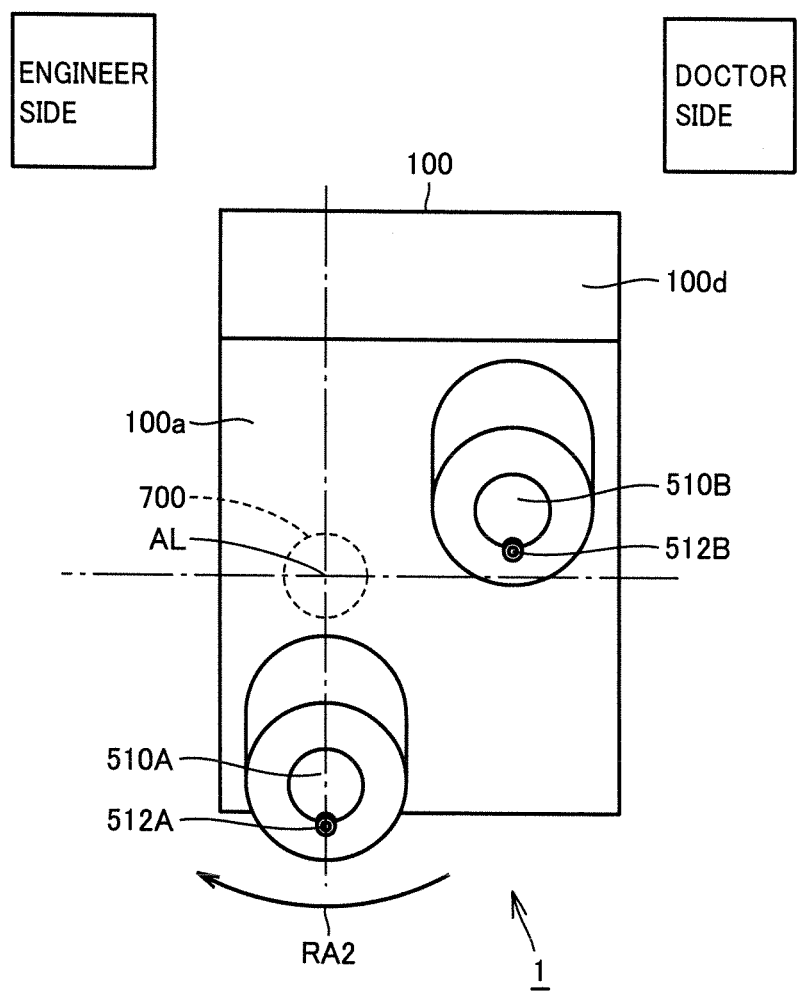
FIG. 30 shows a state of attachment of the injector head with rotation mechanism in accordance with another embodiment.
Figure 31:
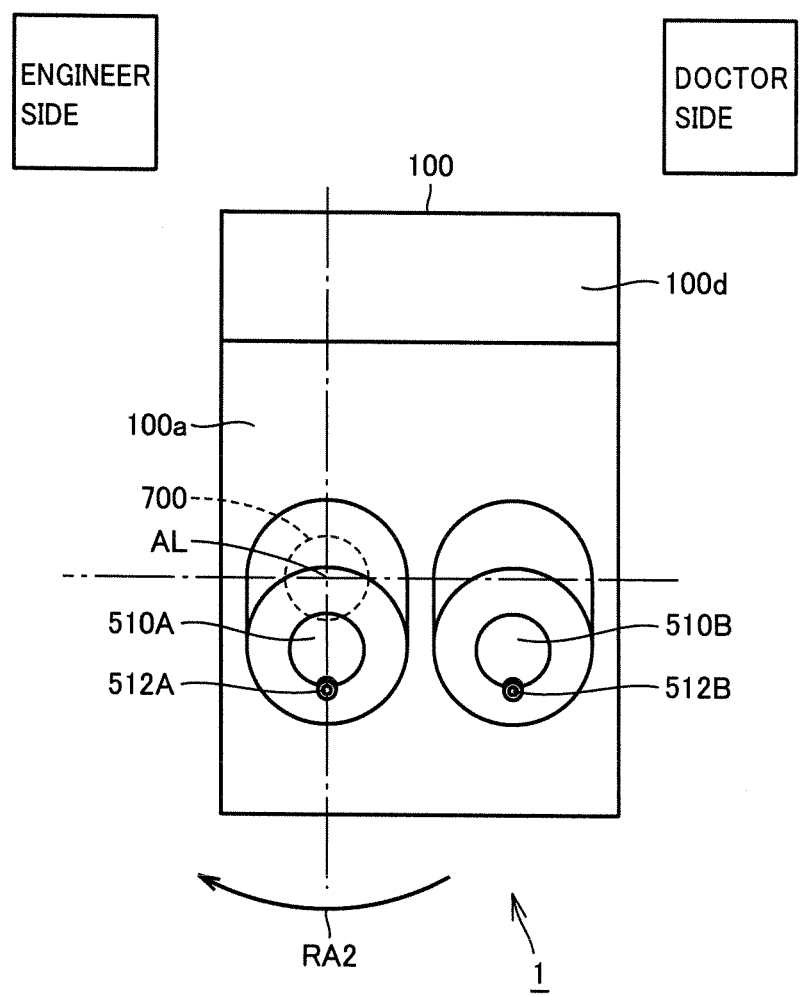
FIG. 31 shows a state of attachment of the injector head with rotation mechanism in accordance with another embodiment.

The state of mounting, however, is not limited to the above. By way of example, when viewed in the contrast agent injectable orientation corresponding to FIG. 4, the state of mounting in which syringes are arranged diagonally with respect to the rotation axis AL such as shown in FIG. 30, the state of mounting in which syringes are arranged side by side in horizontal direction as shown in FIG. 31 or other state of mounting may be adopted.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

REFERENCE SIGNS LIST

1 injector head with rotation mechanism, 10A first tube, 10B second tube, 11A first T-shaped tube, 11B second T-shaped tube, 11C third T-shaped tube, 11D fourth T-shaped tube, 12 coupling tube, 13, 14, 20, 23, 24, 25, 26 connectors, 15 seventh tube, 15A eighth tube, 15B ninth tube, 16 contrast agent bag, 17 main tube, 17a branch tube, 19 normal saline tube, 21 saline bag, 22 tube, 100 injector head body, 100a first surface, 100b second surface, 100c third surface, 100d fourth surface, 100P plunger, 100Pa first plunger, 100Pb second plunger, 110 operation monitor, 111A third tube, 111B fourth tube, 112A fifth tube, 112B sixth tube, 300 blood pressure transducer, 400 roller pump, 510A first syringe, 510B second syringe, 511 piston, 511A first piston, 511B second piston, 511a piston rubber, 511b piston core, 512 through hole, 513 flange, 514 cylindrical part, 600 first flow path switching device, 600A first flow path switching mechanism, 600B second flow path switching mechanism, 601 first fixed valve element, 602 second fixed valve element, 603 first change-over valve element, 604 third fixed valve element, 605 fourth fixed valve element, 606 second change-over valve element, 700 rotating part, 800, 800A second flow path switching devices, 801, 802 fixed valve elements, 803 change-over valve element, 810 main body, 811, 812 fixed valve elements, 811a, 812a fixed projections, 821, 822 movable valve elements, 821a, 822a, 831a, 841a rotation shafts, 821b, 822b movable projections, 831, 841 contact rollers, 851 cover, 851a tube receiving recess, 861, 862 engaging pieces, 870 rotating cam, 900 supporting post, 1000 bed, 2000 patient, 3000 engineer, 4000 doctor, AL rotation axis, AS1 first air sensor, AS2 second air sensor, AS3 third air sensor, L1000 contrast agent injection line, S1 multi-use section, S2, S3 one-time use sections, SL central axis line, Z contrast agent.

The invention claimed is:

1. An injector head with rotation mechanism, comprising:
    a supporting part;
    a rotating part fixed on said supporting part to have a rotation axis extending substantially horizontally;
    an injector head body fixed on said rotating part to be rotatable about said rotation axis; and
    a syringe detachably attached to said injector head body; wherein
    said syringe includes a through hole at a front end side;
    in a state where said syringe is attached to said injector head body, when viewed from the direction perpendicular to and parallel to the rotation axis, central axis line of said syringe is inclined with respect to said rotation axis; and
    the rotating part rotates said injector head body about said rotation axis as the center of rotation to select one of a first state in which said syringe takes a priming orientation with said through hole side of said syringe positioned higher than said injector head body with respect to the rotation axis and a second state in which said syringe takes a contrast agent injectable orientation with said through hole side of said syringe positioned lower than said injector head body with respect to the rotation axis,
    said through hole is provided at a position eccentric to said central axis line of said syringe; and
    said syringe is mounted on said injector head body such that when said syringe is in said priming orientation, said through hole is positioned at the uppermost position, and when said syringe is in said contrast agent injectable orientation, said through hole is positioned at the lowermost position.

2. The injector head with rotation mechanism according to claim 1, wherein
    said injector head body has a substantially rectangular parallelepiped shape;
    said syringe is mounted on a first surface of said injector head body;
    said rotating part is fixed on an upper corner area of a second surface opposite to said first surface;
    in said priming orientation, a third surface positioned on the upper side between said first surface and said second surface is inclined upward from the side of said second surface to the side of said first surface; and
    in said contrast agent injectable orientation with said injector head body rotated about said rotation axis as the center of rotation, a fourth surface positioned on the lower side between said first surface and said second surface is inclined downward from the side of said second surface to the side of said first surface.

3. The injector head with rotation mechanism according to claim 1, wherein
    said syringe has a first syringe and a second syringe;
    said first syringe is mounted on said injector head body such that
    in said priming orientation, when viewed from the direction perpendicular to and parallel to said rotation axis, said central axis line of said first syringe intersects said rotation axis on the side of said through hole of said first syringe, and in said contrast agent injectable orientation, when viewed from the direction perpendicular to and parallel to said rotation axis, said central axis line of said first syringe intersects said rotation axis on the side of said injector head body of said first syringe; and
    said second syringe is mounted on said injector head body such that
    in said priming orientation, when viewed from the direction perpendicular to and parallel to said rotation axis, said central axis line of said second syringe intersects said rotation axis on the side of said injector head body of said second syringe, and in said contrast agent injectable orientation, when viewed from the direction perpendicular to and parallel to said rotation axis, said central axis line of said second syringe intersects said rotation axis on the side of said through hole of said second syringe.

4. The injector head with rotation mechanism according to claim 3, further comprising:
    a tube assembly coupled to the side of a patient; and
    a flow path switching device having one end detachably connected to said tube assembly and the other end connected to said first syringe and said second syringe, for switching said tube assembly to be communicated with said first syringe or with said second syringe; wherein
    said tube assembly is used one time for one patient; and
    said injector head body, said first syringe, said second syringe, and said flow path switching device are used for a plurality of patients.

* * * * *